United States Patent
Adams et al.

(10) Patent No.: US 9,034,618 B2
(45) Date of Patent: May 19, 2015

(54) METHOD FOR SUSTAINING MICROORGANISM CULTURE IN SYNGAS FERMENTATION PROCESS IN DECREASED CONCENTRATION OR ABSENCE OF VARIOUS SUBSTRATES

(75) Inventors: Stephen S. Adams, Fayetteville, AR (US); Syrona Scott, Fayetteville, AR (US); Ching-Whan Ko, Fayetteville, AR (US)

(73) Assignee: INEOS BIO SA, Rolle (CH)

( * ) Notice: Subject to any disclaimer, the term of this patent is extended or adjusted under 35 U.S.C. 154(b) by 602 days.

(21) Appl. No.: 12/381,193

(22) Filed: Mar. 9, 2009

(65) Prior Publication Data

US 2010/0227377 A1    Sep. 9, 2010

(51) Int. Cl.
| | |
|---|---|
| C12P 7/06 | (2006.01) |
| C12P 7/16 | (2006.01) |
| C12N 1/12 | (2006.01) |
| C12N 1/20 | (2006.01) |
| C12P 7/08 | (2006.01) |
| C01B 3/02 | (2006.01) |
| C12P 7/14 | (2006.01) |

(52) U.S. Cl.
CPC ... *C12N 1/20* (2013.01); *C12P 7/16* (2013.01); *C01B 3/02* (2013.01); *C12P 7/14* (2013.01); *C12P 7/065* (2013.01); *C12P 7/08* (2013.01); *Y02E 50/17* (2013.01)

(58) Field of Classification Search
CPC .............. C12P 7/08; C12P 7/065; C12P 7/14; C12P 7/16; C12N 1/20; C01B 3/02; Y02E 50/17
USPC ............................ 435/160, 161, 252.1, 252.7
See application file for complete search history.

(56) References Cited

U.S. PATENT DOCUMENTS

| | | | |
|---|---|---|---|
| 3,180,861 A * | 4/1965 | Kinichiro Sakaguchi et al. ............................ | 540/316 |
| 4,351,905 A | 9/1982 | Clyde | |
| 4,393,136 A | 7/1983 | Cheetham | |
| 4,400,470 A | 8/1983 | Zeikus et al. | |
| 4,654,123 A | 3/1987 | Berg et al. | |
| 4,737,459 A | 4/1988 | Zeikus et al. | |
| 4,886,751 A | 12/1989 | Thorsson | |
| 5,173,429 A | 12/1992 | Gaddy et al. | |
| 5,182,199 A | 1/1993 | Hartley | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,919,488 B2 | 7/2005 | Melnichuk et al. | |
| 7,285,402 B2 * | 10/2007 | Gaddy et al. .................. | 435/161 |
| 2008/0064713 A1 * | 3/2008 | Toyoda et al. | |

FOREIGN PATENT DOCUMENTS

| | | |
|---|---|---|
| WO | WO 98/00558 | 1/1998 |
| WO | WO 00/68407 | 11/2000 |
| WO | WO 2007/123510 A1 | 11/2007 |
| WO | WO 2008/028055 A2 | 3/2008 |
| WO | WO 2008/033812 A2 | 3/2008 |

OTHER PUBLICATIONS

Henstra et al., 2007, Current Opinion in Biotechnology, 18: 200-206.*
Abrini, J., Naveau, H., & Nyns, E.J. (1994). *Clostridium autoethanogenum*, Sp-Nov, an Anaerobic Bacterium That Produces Ethanol from Carbon-Monoxide. *Archives of Microbiology*, 161(4), 345-351.
Bioloen, P., Helle, N.J., & Sachtler, W.M.H. (1979). Incorporation of surface carbon into hydrocarbons during Fischer-Tropsch synthesis: Mechanistic Implication, *Journal of Catalysis*, 58(1), 95-107.
Brady, R.C. & Pettit, R. (1981). On the mechanism of the Fiascher-Tropsch reaction: The chain propagation step. *Journal of American Chemical Society*, 103, 1287-1289.
Bredwell, M.D., Srivastava, P., Worden, R.M. (1999). Reactor Design Issues for Synthesis-Gas Fermentations. *Biotechnol. Prog.* 15, 834-844.
Chang, I.S., Kim, B.H., Kim, D.H., Lovitt, R.W., & Sung. H.C. (1999). Formulation of defined media for carbon monoxide fermentation by *Eubacterium limosum* KIST612 and the growth characteristics of the bacterium. *Journal of Bioscience and Bioengineering*, 88(6), 682-685.
Diekert, G. & Wohlfarth, G. (1994). Metabolism of Homoacetogens. *Antonie Van Leeuwenhoek International Journal of General and Molecular Microbiology*, 66(1-3), 2009-221.
Dry, M.E. (2002). The Fischer-Tropsch process: 1950-20000, *Catalysis Today*, 71(3-4), 227-241.
Girbal, L., Croux, C., Vasconcelos, I., & Soucaille, P. (1995). Regulation of metabolic shifts in *Clostridium acetobutylicum* ATCC 824. *FEMS Microbiology Reviews*, 17(3), 287-297.
Gottschal, J.C., & Morris, J.G. (1981). The Induction of Acetone and Butanol Production in Cultures of *Clostridium acetobutylicum* by Elevated Concentrations of Acetate and Butyrate. *FEMS Microbiology Letters*, 12(4), 385-389.
Harwood, C.S., & Gibson, J. (1988). Anaerobic and aerobic metabolism of diverse aromatic compounds by the photosynthetic bacterium *Rhodopseudomonas palustris* Applied and Environmental *Microbiology*, 54, 712-717.
Hyman M.R. & Arlp, D.J. (1991). Kinetic analysis of the interaction of nitric oxide with the membrane-associated, nickel and iron-sulfur-containing hydrogenase from *Azotobacter vinelandii. Biochimica et Biophysica Acta*, 1076, 165-172.
Jung, G.Y., Jung, H.O., Kim, J.R., Ahn, Y., & Park, S. (1999). Isolation and characterization *Rhodopseudomonas palustris* P4 which utilizes CO with the production of $H_2$. *Biotechnology Letters*, 21(6), 525-529.

(Continued)

*Primary Examiner* — Shin Lin Chen
(74) *Attorney, Agent, or Firm* — INEOS USA LLC

(57) ABSTRACT

The present invention relates to methods for sustaining microorganism culture in a syngas fermentation reactor in decreased concentration or absence of various substrates comprising: adding carbon dioxide and optionally alcohol; maintaining free acetic acid concentrations; and performing the above mentioned steps within specified time.

16 Claims, 3 Drawing Sheets

(56) References Cited

OTHER PUBLICATIONS

Kashket, E.R., :& Zhi-Yi Cao. (1995), Clostridial strain degeneration. *FEMS Microbiology Reviews*, 17(3), 307-315.

Klasson, K.T., Ackerson, M.D., Clausen: E.C., & Gaddy, J.L. (1992) Bioconversion of synthesis gas into liquid or gaseous fuels. *Enzyme and Microbial Technology*, 14(8), 602-608.

Klasson, K.T., Ackerson, M.D., Clausen, E.C., & Gaddy, J.L. (1993). Biological Conversion of Coal and Coal-Derived Synthesis Gas. *Fuel*, 72(12), 1673-1678.

Klasson, K.T., Lundback, K.M.O., Clausen, E.C., :& Gaddy, J.L. (1993). Kinetics of Light Limited Growth and Biological Hydrogen-Production from Carbon-Monoxide and Water by Rhodospirillum-Rubrum. *Journal of Biotechnology*, 29(1-2), 177-188.

Klier, K. (1982), Methanol synthesis. *Advances in Catalysis*, 31, 243-313.

Krasna, A.I. (1979). Hydrogenase: Properties and applications. *Enzyme and Microbial Technology*, 1(3), 165-172.

Krasna, A.I., & Rittenberg, D. (1954). The inhibition of hydrogenase by nitric oxide. *Proceedings of the National Academy of Sciences*, 40(4), 225-227.

Kutzenok, A., & Aschner, M. (1952). Degenerative Processes in a Strain of *Clostridium butylicum*. *Journal of Bacteriology*, 64(6), 829-836.

Lemon, B.J., & Peters, J.W. (1999). Binding of exogenously added carbon monoxide at the active site of the iron-only hydrogenase (Cpl) from *Clostridium pasteurianum*. *Biochemistry*. 38(40), 12969-12973.

Ljungdaht, L.G. (1986). The autotrophic pathway of acetate synthesis in acetogenic bacteria. *Annual Review of Microbiology*, 40, 415-450.

Meyer, C.L., Mclaughlin, J.K., & Papoutsakis, E.T. (1985). The Effect of CO on Growth and Product Formation in Batch Cultures of *Clostridium acetobutylicum*. *Biotechnology Letters*, 7(1), 37-42.

Meyer, C.L., & Papoutsakes, E.T. (1989). Increased Levels of ATP and NADH Are Associated with Increased Solvent Production in Continuous Cultures of *Clostridium acetobutylicum*. *Applied Microbiology and Biotechnology*, 30(5), 450-459.

Meyer, C.L., Roos, J.W., & Papoutsakes, E.T. (1986). Carbon-Monoxide Gasing Leads to Alcohol Production and Butyrate Uptake without Acetone Formation in Continuous Cultures of *Clostridium acetobutylicum, Applied Microbiology and Biotechnology*, 24(2), 159-167.

Misoph, M., & Drake, H.L. (1996). Effect of $CO_2$ on the fermentation capacities of the acetogen *Peptostreptococcus productus* U-1. *Journal of Bacteriology*, 178(11), 3140-3145.

Ragsdale, S. (1991). Enzymology of the Acetyl-CoA Pathway of $CO_2$ Fixation. *Critical Reviews in Biochemistry and Molecular Biology*, 26, 261-300.

Rao, G., & Mutharasan, R. (1989). NADH Levels and Solventogenesis in *Clostridium acetobutylicum*—New Insights through Culture Fluorescence. *Applied Microbiology and Biotechnology*, 30(1), 59-66.

Sarup, B. & Wojciechowski, B.W. (1989). Studies of the Fischer-Tropsch synthesis on a cobalt catalyst. II. Kinetics of carbon monoxide conversion to methane and to higher hydrocarbons. *Canadian Journal of Chemical Engineering*, 67(1), 62-74.

Seefeldt, L.C., & Arp, D.J. (1989). Oxygen Effects on the Nickel-Containing and Iron-Containing Hydrogenase from *Azotobacter vinelandii*. *Biochemistry*, 28(4), 1588-1596.

Steynberg, A.P., Espinoza, R.L., Jager, B., & Vosloo, A.C. (1999). High-temperature Fischer-Tropsch synthesis in commercial practice. *Applied Catalysis, A: General*, 186(1,2), 41-54.

Tibelius, K.H., & Knowles, R. (1984). Hydrogenase activity in *Azospirillum brasilense* is inhibited by nitrite, nitric oxide, carbon monoxide and acetylene. *Journal of Bacteriology*, 160(1), 103-106.

Vasconcelos, I., Girbal, L., & Soucaille, P. (1994). Regulation of Carbon and Electron Flow in *Clostridium acetobutylicum* Grown in Chemostat Culture at Neutral Ph on Mixtures of Glucose and Glycerol. *Journal of Bacteriology*, 176(5), 1443-1450.

Vega, J.L., Clausen, E.C., & Gaddy, J.L. (1990). Design of bioreactors for coal synthesis gas fermentations. *Resources, Conservation and Recycling*, 3(2-3), 149-160.

Vega, J.L., Prieto, S., Elmore, B.B., Clausen, E.C., & Gaddy, J.L. (1989). The Biological Production of Ethanol from Synthesis Gas. *Applied Biochemistry and Biotechnology*, 20-1, 781-797.

Wood, H.G., Ragsdale, S.W., & Pezacka, E. (1986a). The Acetyl-CoA pathway—a Newly Discovered Pathway of Autotrophic Growth. *Trends in Biochemical Sciences*, 11(1), 14-18.

Wood, H.G., Ragsdale, S.,W., & Pezacka, E. (1986b). The Acetyl-CoA Pathway of Autotrophic Growth. *FEMS Microbiology Reviews*, 39(4), 345-362.

Wood, H.G., Ragsdale, S.W., & Pezacka, E. (1986c). A New Pathway of Autotrophic Growth Utilizing Carbon-Monoxide or Carbon-Dioxide and Hydrogen. *Biochemistry International*, 12(3), 421-440.

Zennaro, R., Bartholomew, C.H. and Tagliabue, M. (2000). Kinetics of Fischer-Tropsch synthesis on Titania-supported Cobalt. *Catalysis Today*., 58(4), 309-319.

Liou et al., "*Clostridium carboxidivorans* sp. nov., a Solvent-Producing *Clostridium* Isolated from an Agricultural Setting Lagoon, and Reclassification of the Acetogen *Clostridium scatologenes* strain SL1 as *Clostridium drakei* sp. nov.," Int. J. Sys. Evol. Microbiol., 55:2085-2091 (Sep. 2005).

Klasson et al., "Biological Production of Liquid and Gaseous Fuels from Synthesis Gas" Appl. Biochem. Biotechnol., Proceedings of the 11th Symposium on Biotechnology for Fuels and Chemicals, 24/25:857 (1990).

Phillips et al., "Biological Production of Ethanol from Coal Synthesis Gas-Medium Development Studies" Appl. Biochem. Biotechnol., Proceedings from the 14th Symposium on Biotechnology for Fuels and Chemicals, 39/40:559 (1993).

Rothstein el al., "*Clostridium thermosaccharolyticum* Strain Deficient in Acetate Production," J. Bacteriol, 165(1):319-320 (Jan. 1986).

Lovitt et al., "Ethanol Production by Thermophilic Bacteria: Biochemical Basis for Ethanol and Hydrogen Tolerance in *Clostridum thermohydrosulfuricum*," J. Bacteriol., 170(6):2809 (Jun. 1988).

Taherzadeh et al., "The Effects of Pantothenate Deficiency and Acetate Addition on Anaerobic Batch Fermentation of Glucose by *Saccharomyces cerevisiae*," Appl. Microbiol. Biotechnol., 46:176-182 (Sep. 1996).

Bahl et al., "Continuous Production of Acetone and Butanol by *Clostridium acetobutylicum* in a Two-Stage Phosphate Limited Chemostat," Eur. J. Appln. Microbiol. Biotechnol 15(4):201-205 (Oct. 1982).

Bahl et al., "Nutritional Factors Affecting the Ratio of Solvents Produced by *Clostridium acetobutylicum*," Appl. Environ. Microbiol., 52(1):169-172 (Jul. 1986).

Reardon et al., "Metabolic Pathway Rates and Culture Fluorescence in Batch Fermentations of *Clostridium acetobutylicum*," Biotechnol. Prog., 3(3):153-168 (Sep. 1987).

Terracciano et al., "Intracellular Conditions Required for Initiation of Solvent Production by *Clostridium acetobutylicum*," Appl. and Environ. Microbiol., 52(1):86-91 (Jul. 1986).

Long et al., "Sporulation of *Clostridium acetobutylicum* P262 in a Defined Medium," Appl. Environ. Microbiol., 45(4):1389-1393 (Apr. 1983).

Ferras et al., "Acetonobutylic Fermentation: Improvement of Performances by Coupling Continuous Fermentation and Ultrafiltration," Biotechnol. Bioengin.,28:523 (Apr. 1986).

Clarke et al., "Nature and Significance of Osciliatory Behaviour during Solvent Production by *Clostridium acetobutylicum* in Continuous Culture," Biotechnol. Bioengin., 32:538-544 (Aug. 1988).

Martin et al., "Effects of Acetic and Butyric Acids on Solvent Production by *Clostridium acetobutylicum*," Biotechnol. Lett., 5(20):89-94 (Feb. 1983).

Bryant et al., "Buffering as a Means for Increasing Growth and Butanol Production by *Clostridium acetobutylicum*," J. Indust. Microbiol., 3:49:55 (Feb. 1988).

Husemann et al., "Solventogenesis in *Clostridium acetobutylicum* Fermentations related to Carboxylic Acid and Proton Concentrations," Biotechnol. Bioengin., 32:843-852 (Sep. 1988).

(56) References Cited

OTHER PUBLICATIONS

Barik et al., "Biological Production of Alcohols from Coal through Indirect Liquefaction," Appl. Biochem. Biotechnol., Proceedings of the 9th Symposium on Biotechnol. for Fuels and Chemicals, 18:363 (1988).

Vega et al., "The Biological Production of Ethanol from Synthesis Gas," Appl. Biochem. Biotechnol., Proceedings of the 10th Symposium on Biotechnol. for Fuels and Chemicals, 20/21:781 (1989).

Landuyt et al., Transition from Acid Fermentation to Solvent Fermentatiaon in a Continuous Dilution Culture of *Clostridium thermosaccharolyticum*, Annals of New York Academy of Sciences, pp. 473-478 (Dec. 1987).

Lynd et al., "Thermophilic Ethanol Production," Appl. Biochem. Biotechnol., 28/29: 549 (1991).

DeGraef et al., "The Steady-State Internal Redox State (NADH/NAD) Reflects the External Redox State and is Correlated with Catabolic Adaptation in *Escherichia coli*," J. Bacteriol., 181(8): 2351-2357 (Apr. 1999).

Hols et al.; "Acetate Utilization in *Lactococcus lactis* Deficient in Dehydrogenase: A Rescue Pathway for Maintaining Redox Balance," J. Bacteriol., 181(17):5521 (Sep. 1999).

Rao et al., "Altered Electron Flow in a Reducing Environment in *Clostridium acetobutylicum*," Biotechnol. Lett., 10(2):129-132 (Feb. 1988).

Kim et al., "Redox Potential in Acetone-Butanol Fermentations," 9th Symposium on Biotechnology for Fuels and Chemicals, Boulder, CO (May 5-8, 1987).

Kim et al., "Electron Flow Shift in *Clostridium acetobutylicum* Fermentation by Electrochemically Introduced Reducing Equivalent," Biotechnol. Lett., 10(2):123-128 (Feb. 1988).

Phillips et al., "Synthesis Gas as Substrate for the Biological Production of Fuels and Chemicals," Appl. Biochem. and Biotechnol., Proceedings of the 15th Symposium on Biotechnology for Fuels and Chemicals, 45/46:145 (1994).

Rao et al., "Directed Metabolic Flow with High Butanol Yield and Selectivity in Continuous Culture of *Clostridium acetobutylicum*," Biotechnol. Lett., 10(5):313-318 (May 1988).

Rao et al., "Manipulation of End-Product Distribution in Strict Anaerobes," Annals of New York Academy of Science, pp. 76-83 (Nov. 1987).

Murray et al., "Ethanol Production by a Newly Isolated Anaerobe, *Clostridium saccharolyticum*: Effects of Culture Medium and Growth Conditions," Canad. J. Microbiol., 29:342 (Mar. 1983).

Ram et al., "Ethanol Production by *Clostridium thermocellum* SS8, A Newly Isolated Thermophilic Bacterium," Biotechnol. Lett., 11(8):589-592 (Aug. 1989).

Ingram et al., "Expression of Different Levels of Ethanologenic Enzymes from *Zymomonas mobilis* in Recombinant Strains of *Escherichia coli*," Appl. Environ. Microbiol., 54(2):397-404 (Feb. 1988).

Guedon et al., Carbon and Electron Flow in *Clostridium cellulolyticum* Grown in Chemostat on Synthetic Medium, J. Bacteriol., 181(10):3262-3269 (May 1999).

Grahame et al., "Substrate and Cofactor Reactivity of a Carbon Monoxide Dehydrogenase-Corrinoid Enzyme Complex: Stepwise Reduction of Iron-Sulfur and Corrinoid Centers, the Corrindoid $Co^{2+}/1+$ Redox Midpoint Potential, and Overall Synthesis of Acetyl-CoA," Biochem., 32:10786-10793 (Oct. 12, 1993).

Gottwald et al., "The Internal pH of *Clostridium acetobutylicum* and its Effect on the Shift from Acid to Solvent Formation," Arch. Microbiol., 143:42-46 (Oct. 1985).

Kim, Byung: "Control of Carbon and Electron Flow in *Clostridium acetobutylicum* Fermentations: Utilization of Carbon Monoxide to Inhibit Hydrogen Production and to Enhance Butanol Yields"; Applied and Environmental Microbiology,Oct. 1984; p. 764-770; vol. 48, No. 4; American Society of Microbiology.

Younesi, Habibollah: "Liquid Fuel Production From Synthesis Gas via Fermentation Process in a Continuous Tank Bioreactor (CSTBR) Using *Clostridium ljungdahlii*"; Iranian Journal of Biotechnology, pp. 45-53 vol. 4, No. 1, Jan. 2006.

Younesi, Habibollah: "Ethanol and Acetate Production from Synthesis Gas via Fermentation Processes Using Anaerobic Bacterium, *Clostridium Ljungdahlii*"; Biochemical Engineering Journal 27; School of Chemical Engineering, Universiti Sains Malaysia, Seri Ampangan, Nibong Tebal, Malaysia, Mar. 10, 2005; p. 110-119.

* cited by examiner

Product Concentrations (g/L) and Cell Concentration (g/L) in Reactor, a Straight Through CSTR Used in Feed Gas Loss Experiments - Utilizing CO2 and Ethanol for Energy Product Concentrations (g/L) and Cell Density (g/L) in Reactor, a Straight Through CSTR Used in Loss of Gas with Low Temerature in the Absence of CO2

METHOD FOR SUSTAINING MICROORGANISM CULTURE IN SYNGAS FERMENTATION PROCESS IN DECREASED CONCENTRATION OR ABSENCE OF VARIOUS SUBSTRATES

This invention was made with government support under Grant No. DE-FG36-04GO14315 awarded by the U.S. Department of Energy. The government has certain rights in the invention.

FIELD OF INVENTION

The present invention is directed to improvements in microbial fermentation methods for the production of alcohol from a gaseous substrate containing at least one reducing gas containing at least one acetogenic microorganism.

BACKGROUND OF THE INVENTION

Numerous conventional methods exist for sustaining microorganism culture. However, these methods suffer from numerous inefficiencies. There remains a need for additional more effective methods for sustaining microorganism cultures in the absence of various substrates in a syngas fermentation process.

Three strains of acetogens (Drake, 1994) have been described for use in the production of liquid fuels from syngas: *Butyribacterium* methylotrophicum (Grethlein et al., 1990; Jain et al., 1994b); *Clostridium* autoethanogenum (Abrini et al., 1994); *Clostridium* ljungdahlii (Arora et al, 1995; Barik et al., 1988; Barik et al. 1990; and Tanner et al., 1993). Of these, *Clostridium* ljungdahlii and *Clostridium* autoethanogenum are known to convert CO to ethanol.

U.S. Pat. No. 5,173,429 to Gaddy et al. discloses *Clostridium* ljungdahlii ATCC No. 49587, an anaerobic microorganism that produces ethanol and acetate from CO and $H_2O$ and/or $CO_2$ and $H_2$ in synthesis gas.

U.S. Pat. No. 5,192,673 to Jain et al. discloses a mutant strain of *Clostridium* acetobytylicum and a process for making butanol with the strain.

U.S. Pat. No. 5,593,886 to Gaddy et al. discloses *Clostridium* ljungdahlii ATCC No. 55380. This microorganism can anaerobically produce acetate and ethanol using waste gas (e.g. carbon black waste gas) as a substrate.

U.S. Pat. No. 5,807,722 to Gaddy et al. discloses a method and apparatus for converting waste gases into useful products such as organic acids and alcohols using anaerobic bacteria, such as *Clostridium* ljungdahlii ATCC No. 55380.

U.S. Pat. No. 6,136,577 to Gaddy et al. discloses a method and apparatus for converting waste gases into useful products such as organic acids and alcohols (particularly ethanol) using anaerobic bacteria, such as *Clostridium* ljungdahlii ATCC Nos. 55988 and 55989.

U.S. Pat. No. 6,136,577 to Gaddy et al. discloses a method and apparatus for converting waste gases into useful products such as organic acids and alcohols (particularly acetic acid) using anaerobic strains of *Clostridium* Ijungdahlii.

U.S. Pat. No. 6,753,170 to Gaddy et al. discloses an anaerobic microbial fermentation process for the production of acetic acid.

U.S. Pat. No. 7,285,402 to Gaddy et al. discloses an anaerobic microbial fermentation process for the production of alcohol.

Other strains of aceotgens have also been described for use in the production of liquid fuels from synthesis gas, e.g.: *Butyribacterium* methylotrophicum (Grethlein et al., 1990, Appl. Biochem. Biotech. 24/24:875-884); and *Clostridium* autoethanogenum (Abrini et al., 1994, Arch. Microbiol. 161: 345-351).

There remains a need in the art in preserving culture in syngas fermenation process in decreased concentration or absence of various substrates. There is a need to sustain cultures in the event of various interruptions in industrial process of alcohol production. Particularly, there remains a need to sustain microorganism culture in the event of decreased: CO, H2, or CO and H2 in various concentrations.

SUMMARY OF THE INVENTION

The present invention relates to methods for sustaining microorganism culture in a syngas fermentation reactor in decreased concentration or absence of various substrates comprising: adding carbon dioxide and optionally alcohol; maintaining free acetic acid concentrations; and performing the above mentioned steps within specified time.

The present invention further contemplates a method for preventing rapid loss of microorganism culture in a syngas fermentation reactor in decreased concentration or absence of various substrates comprising: adding carbon dioxide and optionally alcohol; decreasing temperature from the operating temperature; maintaining free acetic acid concentrations; and performing the above mentioned steps within specified time.

The present invention further provides a method for sustaining microorganism culture in a syngas fermentation reactor due to decreased concentration or absence of various substrates in feed gas supply comprising: adding carbon dioxide and optionally alcohol; decreasing temperature from operating temperature; maintaining free acetic acid concentrations; and performing the above mentioned steps within specified time.

As an embodiment of the present invention, alcohol can be utilized as a substrate. Although several alternative growth substrates were tried, none performed as well as alcohol and none are as readily available as the alcohol. When synthesis gas supply is restored the microorganism culture readily returns to utilizing the syngas. Additionally, as an embodiment, solely utilizing the acetate/alcohol pathway does not provide the opportunity for other competing bacteria to grow that may be present in the culture broth or process piping. Whereas a growth substrate such as glucose would be readily available to any organisms present for their growth.

Prior art would include adjustments to the culture broth to maintain a low free acetic acid concentration. These would include raising the pH and increasing the liquid flow to wash out the acetyl. As an embodiment, temperature reduction to reduce culture activity and using the product ethanol and carbon dioxide to provide energy back to the culture to maintain viability. Additionally, the concept of novel alternative substrate.

This is an improvement on the process because there will be times when gas supply is interrupted due to interruptions in gasifier feedstock supply, conveying equipment, drying equipment, gas cleanup or any other unit along the gas supply line. Another application of the present invention comprises transporting innoculum from one site to another. In transport the culture may not not have a syngas supply, therefore an alternative substrate would be required. Having the capability to maintain viability for 12 hours or more would be an improvement in process capability. Therefore, having an alternative that is economically and technically viable will result in minimizing interruptions and/or downturns in alcohol production, plus plant startups and restarts.

DETAILED DESCRIPTION OF THE INVENTION

Definitions

Figure 1:
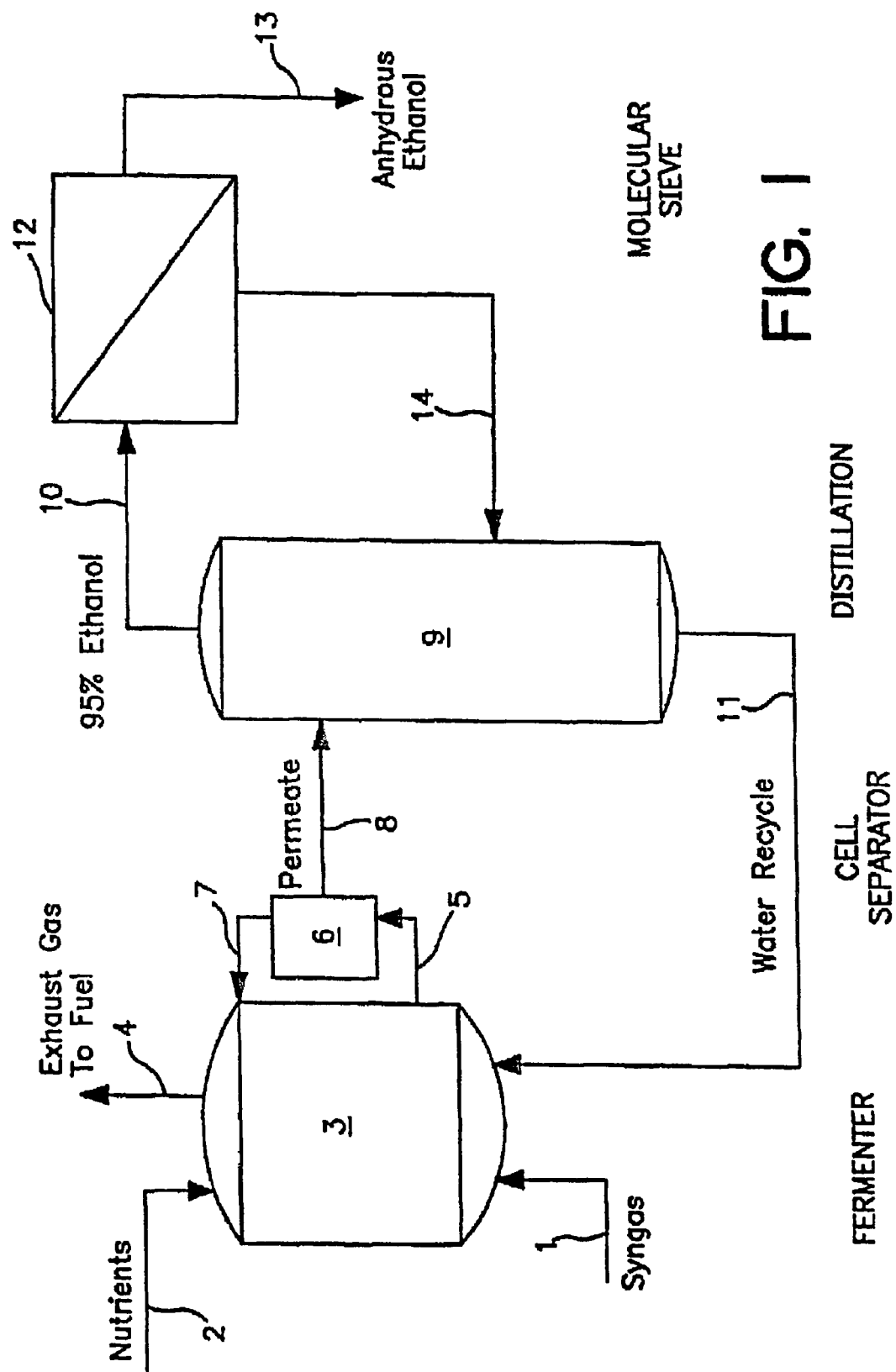
FIG. 1 is a schematic diagram illustrating an embodiment of overall process flow contemplated during normal operations of the present invention. Although ethanol is indicated in the diagram, other alcohols are also contemplated by the present invention.
Figure 2:
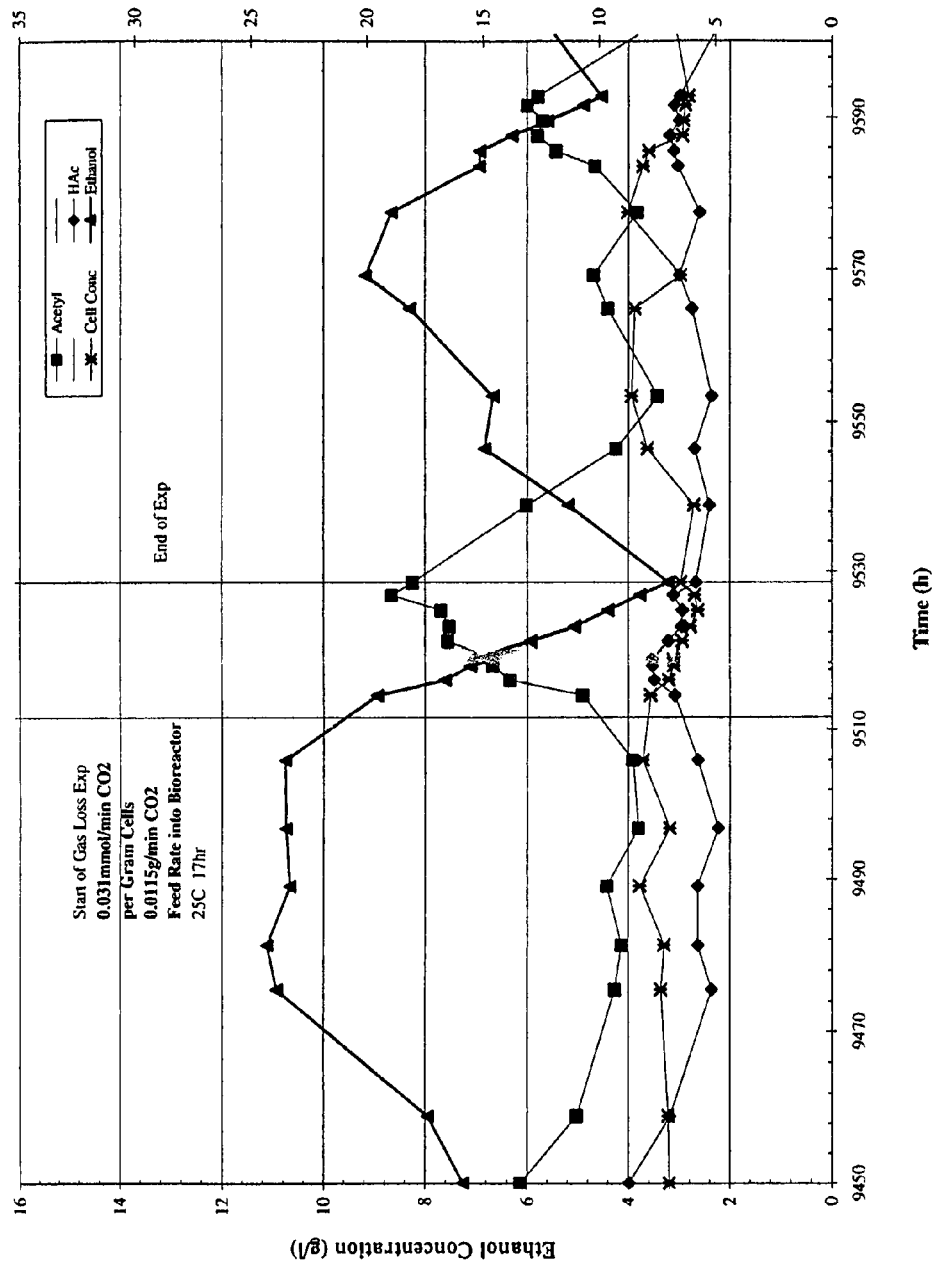
FIG. 2 is a schematic diagram illustrating embodiments of the present invention showing trends with carbon dioxide addition, alcohol consumption, and culture recovery.
Figure 3:
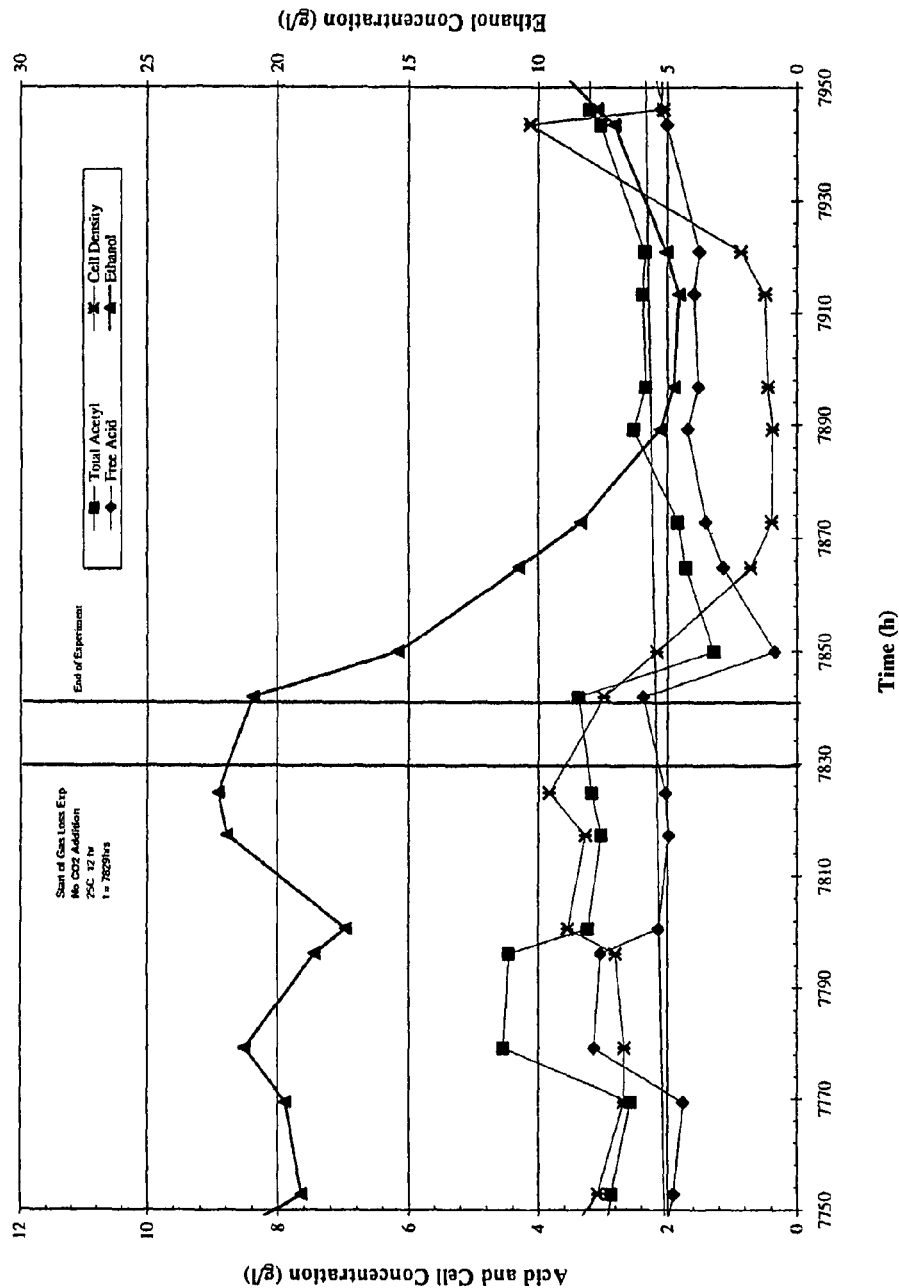
FIG. 3 is a schematic diagram illustrating comparisons of the present invention demonstrating lack of alcohol consumption and lack of culture recovery.

Unless otherwise defined, the following terms as used throughout this specification are defined as follows.

The term "about" modifying any amount refers to the variation in that amount encountered in real world conditions of sustaining microorganism culture, e.g., in the lab, pilot plant, or production facility. For example, an amount of an ingredient employed in a mixture when modified by "about" includes the variation and degree of care typically employed in measuring in an experimental condition in production plant or lab. For example, the amount of a component of a product when modified by "about" includes the variation between batches in an multiple experiments in the plant or lab and the variation inherent in the analytical method. Whether or not modified by "about," the amounts include equivalents to those amounts. Any quantity stated herein and modified by "about" can also be employed in the present invention as the amount not modified by "about."

Unless stated otherwise, the term "acetate" is used to describe the mixture of molecular or free acetic acid and acetate salt present in the fermentation broth. The ratio of molecular acetic acid to acetate is dependent upon the pH of the system, i.e., at a constant "acetate" concentration, the lower the pH, the higher the molecular acetic acid concentration relative to acetate salt.

The term "acetogen" or "acetogenic" refers to a bacterium that generates acetate as a product of anaerobic respiration. This process is different from acetate fermentation, although both occur in the absence of oxygen and produce acetate. These organisms are also referred to as acetogenic bacteria, because all known acetogens are bacteria. Acetogens are found in a variety of habitats, generally those that are anaerobic (lack oxygen). Acetogens can use a variety of compounds as sources of energy and carbon; the best studied form of acetogenic metabolism involves the use of carbon dioxide as a carbon source and hydrogen as an energy source.

The terms "bioreactor," "reactor," or "fermentation bioreactor," include a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact. Preferably for the method of this invention, the fermentation bioreactor comprises a growth reactor which feeds the fermentation broth to a second fermentation bioreactor, in which most of the product, ethanol, is produced.

"Cell concentration" in this specification is based on dry weight of bacteria per liter of sample. Cell concentration is measured directly or by calibration to a correlation with optical density.

The term "continuous method" as used herein refers to a fermentation method which includes continuous nutrient feed, substrate feed, cell production in the bioreactor, cell removal (or purge) from the bioreactor, and product removal. This continuous feeds, removals or cell production may occur in the same or in different streams. A continuous process results in the achievement of a steady state within the bioreactor. By "steady state" is meant that all of these measurable variables (i.e., feed rates, substrate and nutrient concentrations maintained in the bioreactor, cell concentration in the bioreactor and cell removal from the bioreactor, product removal from the bioreactor, as well as conditional variables such as temperatures and pressures) are constant over time.

"Ethanol productivity" is the volumetric productivity of ethanol, calculated as the ratio of the steady state ethanol concentration and the liquid retention time (LRT) in continuous systems, or the ratio of the ethanol concentration and the time required to produce that concentration in batch systems. The phrase "high ethanol productivity" describes a volumetric ethanol productivity of greater than 10 g/L.day.

"Excess $H_2$" is available for ethanol production when the ratio of the moles of $H_2$ in the feed gas to the sum of two times the moles of CO converted and three times the moles of $CO_2$ converted is greater than 1.0. If this ratio is less than 1.0, excess $H_2$ is not available and ethanol can only be produced through a different controlling mechanism.

The term "fermentation" means fermentation of CO to alcohols and acetate. A number of anaerobic bacteria are known to be capable of carrying out the fermentation of CO to alcohols, including butanol and ethanol, and acetic acid, and are suitable for use in the process of the present invention. Examples of such bacteria that are suitable for use in the invention include those of the genus *Clostridium*, such as strains of *Clostridium* lungdahlii, including those described in WO 00/68407, EP 117309, U.S. Pat. Nos. 5,173,429, 5,593,886, and 6,368,819, WO 98/00558 and WO 02/0843, and *Clostridium* autoethanogenum (Aribini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). The disclosures of each of these publications are fully incorporated herein by reference. In addition, other acetogenic anaerobic bacteria may be selected for use in the process of the invention by a person of skill in the art. It will also be appreciated that a mixed culture of two or more bacteria imay be used in the process of the present invention. One micro-organism suitable for use in the present invention is *Clostridium* autoethanogenum that is available commercially from DSMZ and having the identifying characteristics of DSMZ deposit number DSMZ 10061. The fermentation may be carried out in any suitable bioreactor, such as a. continuous stirred tank reactor (CTSR), a bubble column reactor (BCR) or a trickle bed reactor (TBR). Also, in some preferred embodiments of the invention, the bioreactof may comprise a first, growth reactor in which the micro-organisms are cultured, and a second, fermentation reactor, to which fermentation broth from the growth reactor is fed and in which most of the fermentation product (ethanol and acetate) is produced.

The term "gaseous substrates" as used herein means CO alone, CO and $H_2$, $CO_2$ and $H_2$, or CO, $CO_2$ and $H_2$, optionally mixed with other elements or compounds, including nitrogen and methane in a gaseous state. Such gaseous substrates include gases or streams, which are typically released or exhausted to the atmosphere either directly or through combustion. In some embodiments of this method the gaseous substrate comprises CO. In other embodiments of this method, the gaseous substrate comprises $CO_2$ and $H_2$. In still other embodiments, the gaseous substrate comprises CO and $H_2$. In a particularly preferred embodiment, the gaseous substrate comprises CO, $CO_2$ and $H_2$. Still other substrates of the invention may include those components mentioned above and at least one gas of nitrogen, $CO_2$, ethane and methane. Thus, such substrates include what is conventionally referred to as "syngas" or synthesis gas from the gasification of carbon products (including methane), as well as waste gases from a variety of industrial methods.

The phrase "high concentration of ethanol" means greater than about 10 g/L, preferably greater than 15 g/L ethanol in fermentation broth or a product ratio of ethanol to acetate of 5:1 or more.

The terms "limiting substrate" or "limiting nutrient" define a substance in the nutrient medium or gaseous substrate which, during bacterial culture growth in the bioreactor, is depleted by the culture to a level which no longer supports steady state or stable bacterial growth in the bioreactor. All other substances in the nutrient medium or gas substrate are thus present in excess, and are "non-limiting". The evidence for limitation is that an increase in the rate of addition of the limiting substrate, i.e. in the nutrient feed rate or gas feed rate, to the culture causes a corresponding increase in the rate of gas uptake (mmol/min of gas) due to increase in cell density.

The term "microorganism" includes bacteria, fungi, archaea, and protists; microscopic plants (called green algae); and animals such as plankton, the planarian and the amoeba. Some also include viruses, but others consider these as non-living. Microorganisms live in all parts of the biosphere where there is liquid water, including soil, hot springs, on the ocean floor, high in the atmosphere and deep inside rocks within the Earth's crust. Microorganisms are critical to nutrient recycling in ecosystems as they act as decomposers. Microbes are also exploited by people in biotechnology, both in traditional food and beverage preparation, and in modern technologies based on genetic engineering. It is envisioned that mixed strain microorganisms, that may or may not contain strains of various microorganisms, will be utilized in the present invention. In is further envisioned that recombinant DNA technology can create microorganisms using select strains of existing microorganisms. In some embodiments of the present invention, several exemplary strains of C. ljungdahlii include strain PETC (U.S. Pat. No. 5,173,429); strain ERI2 (U.S. Pat. No. 5,593,886) and strains C-01 and O-52 (U.S. Pat. No. 6,136,577). These strains are each deposited in the American Type Culture Collection, 10801 University Boulevard, Manassas, Va. 20110-2209, under Accession Nos.: 55383 (formerly ATCC No. 49587), 55380, 55988, and 55989 respectively. Each of the strains of C. ljungdahlii is an anaerobic, gram-positive bacterium with a guanine and cytosine (G+C) nucleotide content of about 22 mole %. These bacteria use a variety of substrates for growth, but not methanol or lactate. These strains differ in their CO tolerance, specific gas uptake rates and specific productivities. In the "wild" strains found in nature, very little ethanol production is noted. Strains of C. ljungdahlii operate ideally at 37.degree. C., and typically produce an ethanol to acetyl (i.e. which refers to both free or molecular acetic acid and acetate salts) product ratio of about 1:20 (1 part ethanol per 20 parts acetyl) in the "wild" state. Ethanol concentrations are typically only 1-2 g/L. While this ability to produce ethanol is of interest, because of low ethanol productivity the "wild" bacteria cannot be used to economically produce ethanol on a commercial basis. With minor nutrient manipulation the above-mentioned C. ljungdahlii strains have been used to produce ethanol and acetyl with a product ratio of 1:1 (equal parts ethanol and acetyl), but the ethanol concentration is less than 10 g/L, a level that results in low productivity, below 10 g/L.day. In addition culture stability is an issue, primarily due to the relatively high (8-10 g/L) concentration of acetyl (2.5-3 g/L molecular acetic acid) in combination with the presence of ethanol. Furthermore, as the gas rate is increased in an effort to produce more ethanol, the culture is inhibited, first by molecular acetic acid and then by CO. As a result, the culture becomes unstable and fails to uptake gas and produce additional product. Further, early work by the inventors showed difficulty in producing more than a 2:1 ratio of ethanol to acetyl in a steady state operation. See, e.g., Klasson et al., 1990 Applied Biochemistry and Biotechnology, Proceedings of the 11.sup.th Symposium on Biotechnology for Fuels and Chemicals, 24/25: 857; Phillips et al., 1993 Applied Biochemistry and Biotechnology, Proceedings of the 14.sup.th Symposium on Biotechnology for Fuels and Chemicals, 39/40: 559, among others. A large number of documents describe the use of anaerobic bacteria, other than C. ljungdahlii, in the fermentation of sugars that do not consume CO, $CO_2$ and $H_2$ to produce solvents. In an attempt to provide high yields of ethanol, a variety of parameters have been altered which include: nutrient types, microorganism, specific addition of reducing agents, pH variations, and the addition of exogenous gases. See, e.g., Rothstein et al, 1986 J. Bacteriol., 165(1):319-320; Lovitt et al, 1988 J. Bacteriol., 170(6):2809; Taherzadeh et al, 1996 Appl. Microbiol. Biotechnol., 46:176.

By the term "mixed strains," it is meant a mixed culture of two or more of the microorganism. Such "mixed strains" of the microorganism enumerated hereinabove are utilized in the methods of this invention.

The term "natural state" describes any compound, element, or pathway having no additional electrons or protons that are normally present. Conversely, the term "reduction state" describes any compound, element, or pathway having an excess of one or more electrons. The "reduction state" is achieved by adding one or more electrons to the "natural state", i.e. by lowering the redox potential of the fermentation broth.

"Nutrient medium" is used generally to describe conventional bacterial growth media which contain vitamins and minerals sufficient to permit growth of a selected subject bacteria. Sugars are not included in these media. Components of a variety of nutrient media suitable to the use of this invention are known and reported in prior publications, including those of the inventors. See, e.g. the nutrient media formulae described in International Patent Application No. WO08/00558; U.S. Pat. Nos. 5,807,722; 5,593,886, and 5,821,111, as well as in the publications identified above. According to the present invention, a typical laboratory nutrient medium for acetate production from CO, $CO_2$, and $H_2$ contains 0.9 mg/L calcium pantothenate. However, a typical laboratory nutrient medium for ethanol production from CO, $CO_2$, and $H_2$ contains 0.02 mg/L calcium pantothenate.

The term "reducing gas" means either or both CO or $H_2$. By the phrase "an amount of reducing gas greater than that required for growth of the bacteria" is mean that amount of reducing gas that exceeds the amount that the bacteria can use for growth or metabolism, given the nutrient medium ingredients. This amount can be achieved by increasing the net amount of reducing gas, or by reducing key nutrient ingredients, so that the excess amount of gas is achieved without increasing the gas, or by increasing the rate of gas delivery to the bacteria. When the bacteria are exposed to more reducing gas than required for growth, the bacteria respond by increasing the producing of ethanol. "Subject bacteria" are acetogenic anaerobic (or facultative) bacteria, which are able to convert CO and water or H.sub.2 and CO.sub.2 into ethanol and acetic acid products. Useful bacteria according to this invention include, without limitation, Acetogenium kivui, Acetobacterium woodii, Acetoanaerobium noterae, *Clostridium* aceticum, *Butyribacterium* methylotrophicum, C. acetobutylicum, C. thermoaceticum, Eubacterium limosum, C. ljungdahlii PETC, C. ljungdahlii ERI2, C. ljungdahlii C-01, C. ljungdahlii O-52, and Peptostreptococcus productus. Other acetogenic anaerobic bacteria are selected for use in these methods by one of skill in the art.

The term "syngas" means synthesis gas which is the name given to a gas mixture that contains varying amounts of carbon monoxide and hydrogen. Examples of production methods include steam reforming of natural gas or liquid hydrocarbons to produce hydrogen, the gasification of coal and in some types of waste-to-energy gasification facilities. The name comes from their use as intermediates in creating synthetic natural gas (SNG) and for producing ammonia or methanol. Syngas is also used as an intermediate in producing synthetic petroleum for use as a fuel or lubricant via Fischer-Tropsch synthesis and previously the Mobil methanol to gasoline process. Syngas consists primarily of hydrogen, carbon monoxide, and very often some carbon dioxide, and has less than half the energy density of natural gas. Syngas is combustible and often used as a fuel source or as an intermediate for the production of other chemicals Detailed Embodiments of the Present Invention The present invention relates to methods for sustaining microorganism culture in a syngas fermentation reactor in decreased concentration or absence of various substrates comprising: adding carbon dioxide and optionally alcohol; maintaining free acetic acid concentration to less than 5 g/L free acetic acid; and performing the above mentioned steps within 0-30 minutes, within 0-15 minutes, within 15-30 minutes.

The present invention further contemplates a method for preventing rapid loss of microorganism culture in a syngas fermentation reactor in decreased concentration or absence of various substrates comprising: adding carbon dioxide and optionally alcohol; decreasing temperature from the operating temperature to between 0-25 degrees C. while maintaining the temperature between 0-25 C; maintaining free acetic acid concentration to less than 5 g/L free acetic acid; and performing the above mentioned steps within 0-30 minutes, within 0-15 minutes, within 15-30 minutes.

The present invention further provides a method for sustaining microorganism culture in a syngas fermentation reactor due to decreased concentration or absence of various substrates in feed gas supply comprising: adding carbon dioxide and optionally alcohol; decreasing temperature from operating temperature to between 0-25 degrees C. while maintaining the temperature between 0-25 C; maintaining free acetic acid concentration to less than 5 g/L free acetic acid; and performing the above mentioned steps within 0-30 minutes, within 0-15 minutes, within 15-30 minutes.

As an embodiment, said sustaining microorganism culture comprises duration of about 0-30 hours. As an embodiment, pH which can be maintained in the range of about 3.5-5.6. It is further contemplated that a bicarbonate solution is added to control pH. Bicarbonate solution can comprise: ammonium bicarbonate, sodium bicarbonate, and/or potassium bicarbonate. An embodiment of the present invention provides a method wherein optionally removing said carbon dioxide into the said reactor. Furthermore, as an embodiment, optionally adding nutrients to said reactor is provided. The present invention provides optionally adding nutrients to said reactor.

Further embodiments of the present invention provide alcohol comprising one or more of the following: ethanol, butanol, ethanol and butanol.

Optionally, the temperature can be decreased from the operating temperature to between 0-25 degrees C. while maintaining the temperature between 0-25 C; optionally water can be added to said reactor. This water can comprise fresh water, make-up water, recycle water, distilled water, deionized water or their combinations.

The present invention contemplates a method wherein said microorganism culture contains at least one acetogenic bacteria. The microorganism culture can comprise one or more strains selected from *Clostridium, Moorella,* and *Carboxydothermus* or their genetic modifications.

As an embodiment, the microorganism can comprise *Clostridium* ljungdahlii selected from the strains consisting of PETC, ERI-2, O-52 and C-01 or their combinations.

The present invention also provides a method wherein microorganism culture is returned to pre suspension conditions comprising addition of syngas.

Optionally as embodiments, the present invention, can provide for: removing permeate; purging said reactor with inert gas; or maintaining low agitation to keep solids in suspension.

Other aspects and advantages of the present invention are described further in the following detailed description.

Acetogenic autotrophic bacteria that utilize carbon monoxide and/or hydrogen and carbon dioxide (synthesis gas) to produce alcohol require a constant supply of the gas to produce alcohol. An interim product in the production of ethanol is acetic acid, which may be intercellular and extracellular. Without a sufficient synthesis gas supply, limited alcohol is produced in favor of acetic acid.

During conditions when there is reduced or no synthesis gas available for production of the interim product, acetic acid, the culture can convert alcohol back to acetic acid in the presence of carbon dioxide. Ethanol is already present in the culture broth and is readily available in the event of limited or no synthesis gas. Additional alcohol could also be supplied as needed. Carbon dioxide can be added by bubbling the CO2 gas into the culture or it can be formed in the culture broth by the addition of bicarbonate. Sodium bicarbonate can be used in the fermentation to maintain the desired pH and is therefore readily available. In the acidic culture broth the bicarbonate buffer reacts to form carbon dioxide. The formed carbon dioxide is then available to the bacterium to shift alcohol back to acetic acid.

The shift of alcohol to free acetic acid in the presence of carbon dioxide is a relatively fast process. Microorganisms such as *Clostridium* ljungdahlii are limited in the concentration of free acetic acid that can be withstood in the culture broth. Steps need to be taken to control the concentration of free acetic acid during the reduction or loss of synthesis gas. One such method of control is with temperature manipulation. Increased temperature, within the mesophilic range, increases culture activity rates. Whereas reduced temperature in the fermentation broth reduces those rates. Therefore reducing temperature is helpful in retarding the activity of the culture during reduced or no gas conditions, resulting in a slower acid production. Another method of free acetic acid control is changing the culture pH. The equilibrium of acetyl to acetic acid is controlled in part by pH. Raising the pH during synthesis gas supply interruption permits the total acetyl concentration, acetyl plus acetic acid, to be higher while maintaining a lower free acid concentration.

A third method with the potential for controlling the free acid concentration is an increased liquid flow through the system. As the free acid concentration increases, increasing the flow of a liquid stream into the system with an increase in the permeate purge will wash more free acid out of the culture while preventing unwanted cell washout. The additional liquid into the system may be an additional water stream or an increase in the flow of the nutrient supply stream.

Detailed Description of the Process Under Normal Operating Conditions

The present invention involves methods for the anaerobic fermentation of gaseous substrates containing at least one reducing gas, particularly the gaseous components of industrial waste and synthesis gases (e.g., CO, $CO_2$ and $H_2$) to ethanol. These methods yield ethanol productivities greater than 10 g/L.day by manipulating the biological pathways of the subject bacteria. One method of the invention causes an abundance of NAD(P)H over NAD(P). The oxidation of NAD(P)H to NAD(P) causes acetic acid produced by the culture to be reduced to ethanol. Alternatively, other methods for the production of high concentrations of ethanol in an anaerobic fermentation of this invention involve reducing the redox potential of the fermentation broth, and thereby reducing acetic acid to ethanol. The methods of this invention produce high ethanol concentrations (i.e., greater than about 10 g/L, and preferably greater than about 15 g/L) and low acetate concentrations (i.e. less than about 5 g/L free acetic acid in the bioreactor). These methods also maintain and control method conditions for continuous ethanol and acetic acid production to help the system recover rapidly from method upsets. Further, the methods of this invention help prevent culture acclimation to low nutrient concentration, which can be detrimental to culture performance. The present invention provides a viable commercial method for ethanol production.

The Biological Pathways Utilized in the Method of this Invention Under Normal Operating Conditions Without wishing to be bound by theory, the inventors theorize that the methods for increasing the anaerobic production of ethanol from the methods described herein are based upon the biological pathways involving the conversion of NAD (P)H to NAD(P) in the basic pathway cycles of the acetogenic pathway for autotrophic growth. The invention involves manipulating those pathways to enable continuous production and maintenance of high concentrations of ethanol with low acetate concentrations under stable operating conditions, thereby providing commercially useful methods for ethanol production from industrial gases. The essential involvement of NAD(P)H to NAD(P) in the biological pathways is described as follows: The production of ethanol from gaseous components, such as CO, $CO_2$, and $H_2$ occurs in a three step biological method. In the first step, the substrates CO and $H_2$ are oxidized and, in doing so, release NAD (P)H: NAD(P).fwdarw.NAD(P)H CO+$H_2$+$H_2O$.fwdarw.$CO_2$+4$H^+$ The products of step 1 are then converted to acetic acid, a step that requires NAD(P)H: NAD(P)H.fwdarw.NAD(P) CO+$CO_2$+6 $H^+$.fwdarw.$CH_3COOH$+$H_2O$ Finally, if excess NAD(P)H is available because the reaction of step 1 proceeds at a faster rate than the reaction of step 2, acetic acid is reduced to ethanol. NAD(P)H.fwdarw.NAD(P) $CH_3COOH$+4 $H^+$.fwdarw.$C_2H_5OH$+$H_2O$ Thus, the availability of excess NAD(P)H from substrate oxidation leads to the production of ethanol from acetic acid.

There are two known basic pathway cycles in the acetogenic pathway: (1) the Acetyl-CoA cycle and (2) the THF cycle, in which $CO_2$ is reduced to a methyl group. The sequence for the generation of ethanol and acetic acid therefrom is illustrated in J. R. Phillips et al, 1994 Applied Biochemistry and Biotechnology, 45/46:145. The Acetyl-CoA cycle has an inner cycle, referred to herein as the CO cycle. As the CO cycle normally reacts clockwise, ferredoxin is reduced. Ferredoxin can also be reduced by $H_2$ as it is oxidized on the enzyme hydrogenase. As a result, the Acetyl-CoA cycle also reacts clockwise, and ferredoxin is oxidized. If the inner CO cycle and the Acetyl-CoA cycle react at the same rates, ferredoxin is in a redox-state equilibrium. If however, these two cycles do not occur at the same rate, i.e., the CO cycle reacts at a faster rate than the Acetyl-CoA cycle, reduced ferredoxin is built up. Also with excess $H_2$, reduced ferredoxin can also be produced in excess. This excess reduced ferredoxin causes the NAD(P) to be regenerated (reduced) to NAD(P)H, which builds an excess that must be relieved to equilibrium and in doing so, reduces acetic acid to ethanol.

The THF cycle functions for cell growth and is necessary for a continuous culture; therefore it cannot be completely stopped. Reducing the THF cycle rate also serves to cause a higher NAD(P)H to NAD(P) ratio. NAD(P)H is oxidized in two places. By limiting this oxidation, which would keep the total cellular NAD(P)H to NAD(P) ratio in balance, the NAD (P)H is used to reduce acetic acid to ethanol.

A second basic method of causing acetic acid to be reduced to ethanol is by directly lowering the redox potential of the fermentation broth. A reduction state sufficiently lower than the natural state of the culture causes NAD(P)H to be in abundance and promote the reduction of acetic acid to ethanol.

The Methods of the Normal Operation

The basic steps of the method include the following: A continuous fermentation method with product recovery is described by reference to FIG. 1. A continuous flow of gaseous substrate 1 comprising at least one reducing gas, e.g., CO or $H_2$, is supplied at a selected gas feed rate and a continuous flow of liquid phase nutrient medium 2 at a selected nutrient feed rate are supplied to a fermentation bioreactor 3 containing a subject bacteria. In the bioreactor 3, the medium and gaseous substrate are fermented by the bacteria to produce ethanol and acetate acid. Once a stable cell concentration is achieved under steady state conditions, the components of the continuous system are manipulated to reduce the redox potential, or increase the NAD(P)H to NAD (P) ratio, in the fermentation broth, while keeping the free acetic acid concentration in the bioreactor less than 5 g/L. The methods of this invention are designed to permit and maintain production of ethanol and acetate in the fermentation broth such that the ethanol productivity is greater than 10 g/L.day at an ethanol to acetate ratio of between 1:1 and 20:1. In one embodiment, that ratio is greater than 3:1. In another embodiment, that ratio is greater than 5:1. In still another embodiment, that ratio is greater than 10:1. In still another embodiment that ratio is greater than 15:1. The method of this invention is alternatively effective in enhancing stable continuous (steady state) production of high ethanol concentrations (15-35 g/L ethanol) and low acetate concentrations (0-5 g/L acetate), i.e., ethanol to acetate product ratio of 3:1 or more, from CO, $CO_2$, and $H_2$ with good method stability.

Periodically, during the course of the methods of this invention, samples of the broth are removed to determine the ratio by a conventional assay method. For example, the cells are separated from the sample, e.g., by centrifugation and the cell-free sample is then subject to an assay method, such as the preferred method of gas chromatography. However, other conventional assay methods are selected by one of skill in the art. The additional optional steps of the method are added to achieve and/or maintain the ratio.

Steps used to manipulate the system components and maintain and/or achieve the desired ethanol productivity or the ethanol to acetate ratio include at least one, and desirably, combinations of the following steps: altering nutrient medium contents, nutrient feed rate, aqueous feed rate, operating pressure, operating pH, gaseous substrate contents, gas feed rate, fermentation broth agitation rate, avoiding product inhibition step, decreasing cell density in the bioreactor, or preventing substrate inhibition. Some preferred manipulations include supplying the bioreactor with liquid phase nutrient (pantothenate or cobalt) limitation, a slight excess of CO and $H_2$ in the feed gas, minimizing acetate concentration, avoiding culture acclimation to low liquid phase nutrient concentrations, bringing the culture to a suitable cell concentration at a relatively fast rate, raising the pH of the culture above 4.5, purging bacterial cells from the bioreactor to a cell concentration less than the stable steady state concentration that utilizes all reducing gas or nutrient substrates in the bioreactor and increasing the aqueous feed rate when the free acetic acid portion of the acetate present in the fermentation bioreactor broth exceeds 2 g/L, thereby inhibiting any unwanted increase in the concentration of free acetic acid. All of these steps are described in detail below.

Exhaust gas 4 containing gases other than CO, $CO_2$ and $H_2$ and unconverted CO, $CO_2$ and $H_2$ from the reactor are vented from the reactor and are used for their fuel value. If excess $H_2$ as a controlling mechanism is employed, the $H_2$ partial pressure in the outlet gas and ratio of $H_2$ partial pressure to $CO_2$ partial pressure in the exit gas are used to identify the control of the ethanol to acetate ratio by that step. Cell recycle is used (but is not required) to increase the concentration of cells inside the bioreactor, and thus provide more biocatalyst for CO, $CO_2$ and $H_2$ conversion. With cell recycle, liquid effluent from the reactor 5 is sent to a cell separator 6 where the cells 7 and permeate (cell free liquid) 8 are separated. The cells 7 are sent back to the bioreactor and the permeate 8 is sent to product recovery.

Cell separation is accomplished by using a continuous centrifuge, hollow fiber or spiral wound filtration system, ceramic filter system or other solid/liquid separator. Ethanol can be recovered from the permeate (or alternatively the effluent from the reactor 5 if cell separation is not employed) by a variety of techniques including distillation and adsorption. Permeate 8 is separated in a distillation column to produce 95% ethanol overhead 10, and water 11 for recycle back to the reactor 3. The recycle water 11 contains excess nutrients not used in the fermentation, but any excess vitamins from fermentation or cell lysis are destroyed by thermal distillation. The 95% ethanol overhead 10 is sent to a molecular sieve 12 where anhydrous ethanol 13, the desired final product, is separated from dilute ethanol 14 which is sent back to the distillation column 9.

The continuous combination of growth, death and cell purge maintains a constant cell concentration, such that a continuous method used in producing ethanol (and small amounts of acetic acid) can operate for many months by being fed CO, $CO_2$ and $H_2$ along with nutrients without additional culture supplementation. The methods of this invention maintain and control conditions for continuous ethanol and acetic acid production and prevent or correct rapidly for method upsets. The methods of this invention also help prevent culture acclimation to low nutrient concentration, which can be detrimental to culture performance. In the descriptions below and in the examples, unless otherwise indicated, the pressure used is 1 atmosphere and the temperature used is between 36-41.degree. C. Desirable temperatures and pressures may be determined by one of skill in the art, depending on the microorganism selected for use in the bioreactor.

A variety of manipulations, described specifically below, added to the basic steps of this invention permit the enhanced production of ethanol. Preferably, liquid phase nutrient limitation (pantothenate or cobalt) or the use of excess $H_2$ or CO are the method steps of the invention, described in detail below, used to achieve and maintain the desired ethanol productivity and permit production of stable concentrations and ratios of ethanol to acetate in the fermentation broth. These conditions permit production of stable concentrations of ethanol and acetate in the fermentation broth. In a preferred embodiment, the ethanol to acetate product ratio produced in the fermentation broth is greater than 10:1 and the ethanol concentration is greater than 15 g/L.

A. Calcium Pantothenate Limitation

In one specific embodiment of this invention, the method for manipulating the biological pathways to favor ethanol production and limit acetic acid production involves limiting the amount of calcium pantothenate in the nutrient medium to an amount which is less than required to maintain the bacteria at a stable, steady state concentration that would fully utilize the calcium pantothenate provided. Pantothenate is a component of Acetyl-CoA and therefore, by limiting calcium pantothenate in the nutrient medium, the Acetyl-CoA cycle rate is reduced relative to the CO cycle rate. This causes a build-up of reduced ferredoxin and the reduction of NAD(P) to NAD (P)H, and thereby increases the production of ethanol as the final product.

Pantothenate limitation is observed when the micrograms (.mu.g) of calcium pantothenate fed to the reactor per gram (g) of cells (dry weight) produced in the reactor is in the range of 0.5 to 100. A more desirable pantothenate limitation is in the range of 2 to 75 .mu.g of calcium pantothenate per gram (g) of dry cells produced in the reactor. Still a preferred pantothenate limitation is in the range of 0.5 to 50 .mu.g of calcium pantothenate per gram (g) of cells produced in the reactor. Another embodiment of this limitation is at about 1-25 .mu.g of calcium pantothenate per gram (g) of cells produced in the reactor. Another embodiment of this limitation is at about 10-30 .mu.g of calcium pantothenate per gram (g) of cells produced in the reactor. This amount of the nutrient maintains ethanol production in preference to acetate production.

In another aspect of this method, the acclimation of the bacteria in the fermentation bioreactor to low limiting calcium pantothenate concentration is avoided by regulating or adjusting the fermentation parameters, so that a constant calcium pantothenate concentration is maintained, while at least one, and sometimes more than one, parameter of gas feed rate, liquid feed rate, agitation rate, or $H_2$ partial pressure is adjusted. Major changes in nutrients are avoided, but a relatively constant nutrient feed concentration is maintained. If the culture is allowed to acclimate to low liquid phase limiting nutrients, poor product ratios of 1.0 g ethanol/g acetate or less occurs in an irreversible method. Thus, reactor shut down and reinoculation is necessary. Preferably, the biological pathway is controlled to favor ethanol production and limit acetic acid production by first supplying excess $H_2$ in the feed gas to the bioreactor, and then limiting calcium pantothenate in the nutrient medium as described above.

In fact, at start-up, the normally limiting liquid phase nutrient calcium pantothenate is kept in excess to avoid acclimation to low nutrient concentrations, a condition that can result in very poor performance and the loss of the culture's ability to produce achieve high ethanol productivities of more than 10 g/Lday if excess $H_2$ is not employed.

B. Cobalt Limitation

In another embodiment of this invention, the method for manipulating the biological pathways to favor ethanol production and limit acetic acid production involves limiting the amount of cobalt in the nutrient medium to an amount which is less than required to maintain the bacteria at a stable steady state concentration that would fully utilize the cobalt provided. Cobalt limitation is observed when the micrograms ($\mu$g) of cobalt fed to the reactor per gram (g) of cells (dry weight) produced in the bioreactor is in the range of 5 to 100. Preferably, a cobalt limitation involves providing between about 20 to 50 $\mu$g of cobalt to the reactor per gram of cells produced in the reactor. This amount of cobalt maintains ethanol production in preference to acetate in the process.

Limiting cobalt in the fermentation broth may also reduce the Acetyl-CoA cycle rate. Because cobalt is used to transfer a methyl group from the THF cycle to the Acetyl-CoA cycle, limiting the amount of cobalt in the fermentation broth also reduces the THF cycle function by not permitting the transfer. Cobalt limitation reduces the THF cycle rate, which also causes a higher NAD(P)H to NAD(P) ratio, thereby producing ethanol.

The method is further manipulated by preventing acclimation to low limiting cobalt concentration. In much the same manner as acclimation to low pantothenate concentrations is avoided, a constant cobalt concentration is maintained while adjusting one or more of the fermentation parameters (gas rate, liquid rate, agitation rate, $CO_2$ content, and $H_2$ gas partial pressure). Major changes in nutrients is avoided, but instead a relatively constant nutrient feed concentration is maintained.

Preferably, the biological pathway is controlled to favor ethanol production and limit acetic acid production by first feeding excess $H_2$ to the reactor and then limiting cobalt in the nutrient medium as described above. At start-up, the limiting liquid phase nutrient cobalt is kept in excess to avoid acclimation to low nutrients concentration, a condition that can result in very poor culture performance and the loss of the culture's ability to produce product ratios greater than 1:1.

C. Oversupplying Hydrogen

In still another embodiment, the method for manipulating the biological pathways to favor ethanol production and limit acetic acid production involves feeding excess $H_2$ in the feed gas or limiting gaseous carbon which results in excess $H_2$, which is then used by the biological pathway. Preferably, the $H_2$ reducing gas is in excess relative to CO, and the excess $H_2$ causes the bacteria to produce a high ethanol to acetate ratio in the fermentation broth. If the ratio of the $H_2$ (moles of gas fed) to the sum of two times the CO (in moles of gas) converted and three times the $CO_2$ (in moles of gas) converted is greater than 1, the fermenter is carbon limited. The $H_2$ partial present in the exit gas is preferably greater than 0.4 atm. Finally the ratio of $H_2$ partial pressure to $CO_2$ partial pressure must be greater than 3.0 to assure that sufficient $H_2$ is available to use all the $CO_2$. If the $CO_2$ partial pressure is greater than 0.1 atm, it is likely that growth has been otherwise limited.

During start-up, the use of excess $H_2$ is favored over nutrient limitation, mainly because it is easier to control. The benefits of employing excess $H_2$ are that it avoids excess acetic acid production, which can lead to poor product ratios and potential acetic acid inhibition, as well as acclimation to low nutrient concentrations.

D. Oversupplying Carbon Monoxide

Another way of manipulating the components of the method involves oversupplying the reducing gas, CO, in the gaseous substrate for use in the pathway, which serves to directly lower the redox potential in the fermentation broth. Thus, according to this embodiment, the bioreactor is suppled with gaseous substrate comprising CO where the amount of CO present in the bioreactor is greater than the amount required to maintain the bacteria at a stable, steady state concentration that would fully utilized the CO provided. CO oversupply as a method of favoring ethanol production over acetic acid production when the specific rate of CO uptake (millimoles of CO per gram of cells (dry weight) in the reactor per minute, or mmol/g cellmin) is greater than 0.3. More preferably, this step involves a specific rate of CO uptake of greater than 0.5. This means that each cell on the average is utilizing CO in its metabolism at a rate of at least 0.3 mmol/gmin., or more ideally at a rate of at least 0.5 mmol/gmin. Preferably, the CO is provided at a rate at which the CO uptake is from 0.3 to 2 mmol CO/gram cell (dry weight) of bacteria/minute. In another embodiment, the CO is provided at a rate of from 0.5 to 1.5 mmol CO/gram cell (dry weight) of bacteria/minute. In another embodiment, the CO is provided at a rate of about 1 mmol CO/gram cell (dry weight) of bacteria/minute.

This rate of CO uptake maintains ethanol production in preference to acetate production. If CO is supplied such that the dissolved CO in the fermentation broth is significant by gas pressure or extremely good mass transfer, the fermentation broth becomes more reduced. Oversupply of CO has two additional benefits. Excess CO may cause the CO cycle to operate at a faster rate, and if the Acetyl-CoA cycle is otherwise limited and cannot keep up with the CO cycle, reduced ferredoxin builds-up. CO may also slow down step 2 (production of the intermediate acetic acid) in the overall three-step method through substrate inhibition. This decreased rate of step 2 in relation to step 1 causes an excess of NAD(P)H, which leads to ethanol production in favor of acetic acid.

Although excess CO can result in increased ethanol production by directly reducing the redox potential of the fermentation broth, the presence of excess CO also inhibits growth by inhibiting the CO-dehydrogenase and therefore the uptake of $H_2$. The presence of excess CO unfortunately also results in poor $H_2$ conversion, which may not be economically favorable. The consequence of extended operation under substrate inhibition is poor $H_2$ uptake. This eventually causes cell lysis and necessary restarting of the reactor. Where this method has an unintended result of CO substrate inhibition (the presence of too much CO for the available cells) during the initial growth of the culture or thereafter, the gas feed rate and/or agitation rate is reduced until the substrate inhibition is relieved.

E. Additional Manipulating Steps

In addition to the major method enhancing steps described above, several method steps are desirably included in the ethanol production method.

1. Increasing Mass Transfer

One such additional embodiment involves ensuring that the mass transfer of the CO or $H_2$ from the gas feed to the liquid fermentation broth is faster than the ability of the bacteria to utilize the dissolved gases. For example, if a bioreactor containing C. ljungdahlii is fed CO, $CO_2$ and $H_2$ and is operated without limitation on nutrients (such as pantothenate or cobalt) or the presence of excess $H_2$, cell growth is limited by the amount of gas transferred into the liquid phase and the system produces acetic acid as the product. If the culture is fed a slight amount of CO or $H_2$ in excess of that required for culture growth, it produces ethanol. However, if too much gas is transferred into the liquid phase for the culture to use, substrate inhibition occurs, which can lead to culture upset and cell death. Thus, there is a very narrow range of operation with excess mass transfer.

With reference to the Acetyl-CoA cycle, in order for the excess reduced ferredoxin to be produced, the CO cycle or the reduction of ferredoxin through hydrogenase must occur faster than the Acetyl-CoA cycle. The methods described herein limit the rate at which the organisms can utilize the dissolved gases by restricting the rate at which essential nutrients e.g., calcium pantothenate or cobalt, or other substrates, such as $CO_2$ gas, are available to the bacteria, or by providing excess substrate, $H_2$ or CO to the culture.

A theoretical rate of mass transfer, which is faster than the rate at which the bacteria can use substrate, even without other limitations, can be calculated. That rate, when achieved, is limited by the natural growth rate of the organism. Therefore, the most productive embodiment is where the mass transfer (gas flow rate or agitation rate) is faster than the rate at which the highest possible concentration of cells can utilize the substrate without any limitation. There would be a very narrow operating range since substrate inhibition could quickly cause cell death and a resulting by-product concentration which is toxic to the culture.

2. Supplying Excess CO and $H_2$

In another embodiment of a method of this invention, stability in the high ethanol concentration/limited acetic acid production is achieved in the methods which limit cobalt or calcium pantothenate, or provide an abundance of $H_2$ or CO. According to this step, as the culture uses the gaseous substrates CO, $H_2$ and $CO_2$ as the carbon and energy sources, CO and $H_2$ are supplied in slight excess. A slight excess of CO and $H_2$ is achieved by attaining steady operation and then gradually increasing the gas feed rate and/or agitation rate (10% or less increments) until the CO and $H_2$ conversions just start to decline. This is one means of avoiding mass transfer limitation, which favors acetic acid production, and supplying excess reduced ferredoxin in order to reduce NAD(P) to NAD(P)H and produce ethanol. If CO and $H_2$ are not supplied in slight excess, mass transfer limitation occurs, and the pathway is balanced. This results in poor ethanol to acetate product ratios (high acetate concentrations). High acetate concentrations can ultimately result in acetic acid inhibition, which limits the ability of the bacterium to take up $H_2$ and can eventually lead to culture failure.

Steps to avoid mass transfer limitation include an increase in the agitation rate or gas rate to transfer more CO and $H_2$ into the liquid phase, and thus return to the presence of a slight excess CO and $H_2$. If product inhibition occurs as a result of mass transfer limitation, it is necessary to increase the liquid feed rate to clear the acetic acid inhibition, by diluting to a lower resulting acetate concentration. Since increasing the medium feed rate would increase the .mu.g pantothenate or cobalt/g-cell produced, this must be done only briefly or the excess pantothenate or cobalt must be eliminated by adjusting the medium concentration or increasing the water feed rate.

3. Conditioning Acetic Acid Product Inhibition

Where in the methods described above, acetic acid product inhibition can occur if too much molecular acetic acid, i.e., >2 g/L, accumulates in the bioreactor to allow cell growth and further ethanol production. Another manipulating step is used to avoid culture failure. One modification involves briefly increasing the liquid or aqueous feed rate to reduce the liquid phase concentration of inhibiting acetic acid to lower than 2 g/L.

4. Water Recycle Step

Still another optional method step for maintaining a stable culture which produces ethanol as the only product with no net acetic acid production in the methods of this invention involves adding water recycle from distillation back to the fermentation reactor. As was noted earlier, water (containing up to 5 g/L acetate) recycle has the benefit of recycling the produced acetate back to the reactor so that no net acetic acid is produced. An equilibrium is thus established between the ethanol and acetate in the reactor. As a result, all CO, $CO_2$ and $H_2$ fed to the reactor and converted to products results in ethanol production, except for that used for culture maintenance.

5. Reducing Cell Density

Still another manipulating step useful in the method is to initiate periodic or continuous purging of bacterial cells from the bioreactor to reduce the cell concentration in the bioreactor. This manipulation serves to reduce the cell concentration to less than a stable, steady state cell concentration that utilizes all reducing gas or nutrient substrates in the bioreactor. By thus, altering the cell density, the production of ethanol is favored over the production of acetate in the bioreactor.

6. Two Stage CSTR

One of the problems associated with ethanol production with medium limitation is the ability or tendency of the culture to eventually adapt to the limiting conditions and not continue to produce ethanol after several months of operation. Instead acetate iscome eventually the dominant product. This acclimation to low limiting nutrient concentrations results in a culture which produces more acetic acid than ethanol (ethanol to acetate product ratio of 1.0 or less), and yields low ethanol concentrations (sometimes as low as 1 g/L). Adaptation most likely occurs when the culture is not provided with sufficient nutrients during start-up, where growth rate is more important than ethanol production rate. Additionally, there is a danger that the culture can be acclimated to low limiting nutrient concentrations during steady state operation particularly as the limiting nutrient concentrations are adjusted downward to rid the reaction system of acetate.

To avoid this adaptation when using the pantothenate or cobalt limiting steps above, instead of allowing the culture to grow with the available nutrients, and the danger mentioned above, another modification of the method can be employed. A two-stage CSTR system where primarily good culture growth occurs in the first stage on a slight excess of limiting nutrients (perhaps with accompanying acetic acid production), followed by a production stage where the culture from the first stage is now limited by the limiting nutrient and is used to produce high concentrations of ethanol, is another modification of the method. This modification enables the maintenance of a stable culture, which does not acclimate to reduced pantothenate or cobalt concentrations. This modification involves operating a two-stage CSTR, in which a growth reactor (Stage 1) to feed a production reactor (Stage 2) where the bulk of the ethanol production occurs. The growth reactor is not operated with the nutrient limitation steps described above, so the culture is not as susceptible to acclimation to a limited condition.

According an embodiment of two-stage CSTR, the Growth Stage is operated at a liquid retention time (LRT) of about 24 hours. The Growth Stage CSTR 1 is fed enough pantothenate or cobalt in the medium 2 to yield a healthy culture (and may produce some acetic acid as well). Thus, excess acetic acid is produced in the reactor, but with increased stability. This pantothenate or cobalt concentration is in excess of what would normally be fed to a single CSTR used to produce ethanol. The gas feed to this reactor is unconverted gas 3 from the Production Stage 4 and the liquid feed is fresh medium 2. The Growth Stage CSTR is operated without cell recycle. The purpose of this Growth Stage reactor is to provide a healthy culture for later ethanol production that does not acclimate to low pantothenate concentrations.

The Production stage reactor 4 is operated at a nominal LRT of less than 20 hours. This CSTR with cell recycle is fed a fresh gas feed 5, and may have low conversions. It is fed fresh medium feed 6 as well as culture feed 7 from the Growth Stage. Minimal pantothenate or cobalt is fed to this reactor since the excess from the Growth Stage is available. Cell recycle 8 is used in this reactor in order to get the most production out of the cells sent back to the reactor 9. The exit ethanol concentration in the liquid product 10 should be greater than 20 g/L. The features of the two-stage CSTR system include little change for acclimation to low pantothenate or cobalt concentrations; an overall LRT of less than or equal to 30 hours; an expected greater ethanol productivity and higher ethanol concentration than from a single CSTR of the same size.

7. Start-up Modifications

Still other method steps, which are preferably utilized in the practice of this invention, involve cell production in the initial start-up of the fermentation culture. The start-up of a bioreactor fed CO, $CO_2$ and $H_2$ to produce ethanol and acetic acid is accomplished by batch inoculation from stock culture or by employing a continuous inoculum from an existing reactor as culture feed. As noted earlier in the discussion of avoiding culture acclimation to low pantothenate or cobalt concentrations, the culture is most desirably brought up to a high cell concentration prior to limiting nutrients, but supplying excess $H_2$ to the culture. This rapid start-up avoids culture acclimation and yields good product ratios (high ethanol and low acetate concentrations). If the rapid start-up is not employed, poor product ratios can occur and the culture can acclimate to low liquid phase nutrient concentrations and require reactor reinoculation.

The reactor is started with a batch liquid phase (liquid medium is not initially fed continuously to the reactor), at low agitation rates (perhaps 400-600 rpm in a laboratory New Brunswick Scientific Bioflo.®. reactor) and at the desired pH. The liquid phase in the reactor thus consists of a batch of nutrient medium containing vitamins and salts, with a nominal concentration of limiting nutrient, either calcium pantothenate or cobalt (20 .mu.g/L pantothenate or 75 ppb cobalt). If continuous inoculum from an existing reactor is employed, batch liquid phase operation likely is not necessary. In this case, gas is fed continuously to the reactor during initial start-up at a slow rate. Ideally, the gas phase at start-up would be $CO_2$-free, $H_2$-abundant and the gas rate and agitation rate would be kept at low levels to avoid CO substrate inhibition.

An exemplary general start-up protocol for producing and sustaining commercially viable ethanol concentrations from CO, $CO_2$ and $H_2$ consists of three distinct phases: (a) initial start-up, where cell production is critical; (b) start-up where production rate becomes critical; and (c) steady state operation. Essentially, initial start-up is characterized by inoculation of a batch liquid, with a nominal limiting nutrient, selected from cobalt (75 ppb) or calcium pantothenate (20 .mu.g/L) at a desired pH (typically 4.5-5.5). To facilitate start-up, the gas feed rate and agitation rate are preferentially kept low, while $H_2$ is fed in excess. The cause of ethanol production during start-up is excess $H_2$; nutrient limitation occurs later. Thus, excess liquid nutrients are actually present during start-up to avoid unwanted culture acclimation to low nutrients. As the fermentation proceeds over a period of several hours after inoculation, $CO_2$ is produced and $H_2$ is consumed. The changes in these rates indicated that the agitation rate should be nominally increased slowly (perhaps by 200-300 rpm in a laboratory reactor, over a period of 2-3 days) to avoid mass transfer limitation.

This onset of $CO_2$ production occurs much more rapidly in systems employing continuous inoculation as opposed to batch inoculation from stock culture. However, if the agitation rate is increased too fast, CO substrate inhibition occurs. This procedure of watching $H_2$ conversion (or $CO_2$ production) while nominally increasing agitation rate occurs at a relatively rapid rate until the target agitation rate is reached. During this time of increasing agitation rate in batch liquid culture, cell production instead of product formation is of utmost importance.

Once the target agitation rate is reached (800-1000 rpm in laboratory New Brunswick Scientific Bioflo® reactor), the culture is allowed to steady to confirm $H_2$ uptake. The start-up shifts to a mode in which production rate becomes important. It is desirable to have CO conversions exceeding 80% and a high $H_2$ partial pressure in the exit gas (at least 0.55 atm) to assure ethanol production while limiting acetate and the free molecular acetic acid concentration. The liquid medium feed rate is then turned on (for systems having batch inoculation from stock culture) to initiate continuous liquid feed and the gas rate is increased in 10% increments toward the target flow rate. $H_2$ remains in excess to avoid excess acetic acid production. As the gas rate is increased, the liquid phase nutrients are limited (calcium pantothenate or cobalt), and the effect of such limitation is a small drop in $H_2$ conversion, at the target production.

At steady state operation, production of 15-35 g/L ethanol and 0-5 g/L acetate is reached. At this stage, small adjustments in limiting nutrients, liquid feed rates and gas feed rates are needed, and are chosen by one of skill in the art with resort to knowledge extant in the art as well as the teachings of this invention. If cell recycle is to be added to the method of ethanol production, it is added at this time along with an adjustment in gas rate (increase) and nutrient concentration (decrease).

The above described methods of continuously producing and maintaining high concentrations of ethanol with low by-product acetate concentrations under stable operating conditions enhance the use of the subject bacteria on a commercial scale for ethanol production. The steps outlined in the methods above overcome the limitations of utilizing the subject bacteria for commercial ethanol production from CO, $CO_2$ and $H_2$. Preferably the method employs a continuous bioreactor, although batch and fed-batch fermentation methods are also used, but are not likely to be economically viable for large-scale ethanol production.

The following examples will serve to illustrate certain specific embodiments of the inventions herein disclosed. These Examples should not, however, be construed as limiting the scope of the novel invention as there are many variations which may be made thereon without departing from the spirit of the disclosed invention, as those of skill in the art will recognize.

EXAMPLES

An initial experiment was conducted to investigate using ethanol and carbon dioxide as the energy source for maintaining the viability of C. Ljungdahlii. In this experiment the carbon dioxide was provided as a gas bubbled through the culture. The free acid concentration was controlled by lowering the temperature to 25 degrees C. and by increasing the pH set point. The synthesis gas was turned off and replaced with a slow bubbling of carbon dioxide at approximately 30ml/min. Agitation was decreased to a low level that provided just enough mixing to distribute heat and liquid additions into the reactor. The pH was raised from 4.5 to 4.7. The. reactor had a cell recycle loop using a hollow fiber membrane, which permitted a permeate purge to be used in order to prevent cell loss during the experiment. The permeate flow was equal to the flow of medium into the system. The liquid retention time did not change, remaining at 30 hours.

After 12 hours of no synthesis gas supply, the measured ethanol and total acetyl concentrations had changed as was expected. The ethanol level decreased from 24.0 to 12.8g/L while the total acetyl level increased from 4.2 to 10Ag/L. The temperature set point was returned to 38° C. As the culture was heating, the agitation was increased to the same level used prior to the experiment; the carbon dioxide was replaced with synthesis gas flow at 50 percent the flow rate used prior to the experiment.

The permeate purge was stopped. The culture was maintained in this condition for 14 hours. During that time the carbon monoxide uptake remained stable and the hydrogen uptake steadily improved. Once the hydrogen uptake had improved sufficiently, the gas flowrate was stepwise increased to reach the pre-experimental flowrate. Within 47.5 hours the synthesis gas flow rate had returned to pre-experimental rates. As the feed gas flow was increasing, the total acetyl concentration was decreasing and the ethanol concentration increased. The total acetyl concentration was back down to pre-experimental levels within 32 hours. The ethanol concentration reached near pre-experimental levels within 70.5 hours.

In this experiment the carbon dioxide was provided by a continuous flow of a 7.7% sodium bicarbonate solution into the culture. The temperature was reduced to 25° C. Free acetic acid concentration was controlled by lowering the temperature to 25° C., increasing pH and by increasing the liquid flow through the culture. The synthesis gas was turned off and replaced with a continuous flow of 7.7% sodium bicarbonate. In the presence of an acidic environment, sodium bicarbonate degrades into a sodium ion, water and carbon dioxide thus providing the necessary carbon dioxide for the conversion of ethanol to free acid. Agitation was decreased to a low level that provided just enough mixing to distribute heat and liquid additions into the reactor. The pH set point was not controlled, but as the bicarbonate was added to the culture, the pH slowly increased throughout the experiment which helped control the concentration of free acid. The reactor had a cell recycle loop using a hollow fiber membrane, which permitted a permeate purge to be used in order to prevent cell loss during the experiment. The permeate flow was equal to the flow of medium plus the additional flow of sodium bicarbonate into the system. The extra bicarbonate flow reduced the liquid retention time from 29 to 21 hours.

During the experiment the ethanol concentration decreased as the total acetyl concentration rose steadily. Within 5.5 hours the ethanol concentration had decreased from 21.0 to 14.1 g/L while the total acetyl level had increased from 4.4 to 9.1g/L. The measured pH had also increased from 4.48 to 4.84. In an effort to control the acid concentration, the nutrient stream flow rate was increased from 1.33mL/min to 2.81 mL/min., 5.6 hours after the start of the experiment. The permeate purge was also increased from 1.86 to 3.48mL/min to prevent unwanted cell washout. These changes decreased the liquid retention time from 21 to 12 hours. This had the desired effect of holding the acid concentration down. Two hours after the changes in liquid flows the total acetyl concentration had increased to only 9.4g/L. However, the ethanol concentration dropped at a faster rate from 14.1 to 10. 7g/L. After 8 hours of no synthesis gas supply, the measured ethanol and total acetyl concentrations changed as expected. The ethanol level decreased from 21.0 to 10.7g/L while the total acetyl level increased from 4.4 to 9.4g/L. The temperature set point was raised back to 38° C. As the culture was heating, the agitation was increased to the same level used prior to the experiment; the sodium bicarbonate addition was stopped, synthesis gas flow was started at 50 percent the flow rate used prior to the experiment; and the permeate purge was stopped. The culture was maintained in that condition for only 50 minutes. The gas flow rate was stepwise increased to reach the prior flow rate. Within 29.2 hours the synthesis gas flow rate had returned to pre-experimental rates. As the feed gas flow was increasing, the total acetyl concentration decreased and the ethanol concentration increased to pre-experimental concentrations within 43.2 hours. Thus ethanol that is already in the fermenter can thus be used along with carbon dioxide to maintain culture viability during synthesis gas interruption.

Example 1

Microorganism Gas Loss Studies Using Ethanol and CO2 Conversion for Energy

The purpose of the microorganism experimentation was to determine a method of sustaining culture in the event of a feed gas loss for an extended (>30 minute) period of time. In this example, the focus was on CO2 addition for the conversion of ethanol to free acid as a way for the culture to gain energy during the loss of synthesis gas.

It has been known for quite some time that certain acetogenic microorganisms can convert ethanol back to acetic acid using CO2, but no testing had been done to determine if this process could be used to sustain the culture for long periods of time when there was no synthesis gas available. An embodiment of the present invention provides a solution for surviving a loss of feed gas since ethanol and CO2 (in the form of sodium bicarbonate) are readily available for use due to normal bioreactor operations. In addition to adding CO2 for the conversion of ethanol to acid the culture temperature was decreased during some of the experiments as a way to slow culture activity. A slower cell activity should reduce the amount of energy needed, the amount of CO2 and ethanol required, and the amount of acid produced.

For these experiments the bioreactor was run as a straight through CSTR with both a cell recycle and culture cooling coil loop. A permeate purge was used during the experiments to prevent unwanted cell loss, but the purge stream was diverted to waste and was not recycled back into the bioreactor. During the normal bioreactor operations the culture temperature was kept 38° C.; agitation was 400 rpm; the approximate culture volume was about 2.4 L; and the culture pH set point was 4.5. A solution of 7.7% NaHCO3 was used for pH control. The feed gas was synthesis gas containing 15% H2, 45% N2, 30% CO and 10% CO2. The syngas feed rate was about 475mL/min. Medium was fed into the reactor at about 1.30-1.35 mL/min, or about 1870-1940 mL/day. Liquid and cell retention times averaged 25-30 hours. The medium used was the 1× EtOH medium regularly used for the C-01 culture. Medium components and their concentrations are listed in Table 1 below.

During normal operations the CL bacteria use the syngas components CO, $H_2$ and $CO_2$ as substrates for its carbon and energy, or electron, source. Because of that, care must be taken to prevent the loss of that substrate in order to sustain the culture. However, should the feed gas supply be interrupted, the bacteria can survive by utilizing ethanol and CO2 to produce acetic acid as seen in Equation (1) below.

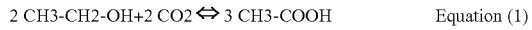

Equation (1)

Through this reaction, the cells can advantageously gain electrons for survival from the oxidation of the alcohol to the carboxylic acid form. If feed gas is interrupted, the culture typically gains electrons, while not gaining carbon thus decreasing cell growth. It is therefore believed that this process provides a means of culture survival, though not optimized production. Cell washout, or the removal of any cells from the system, should be avoided in order to maintain the cell density during the feed gas loss.

This process leads to a buildup of acid. Steps must be taken to insure that the free acetic acid levels are maintained to concentration levels below inhibiting concentrations (≤5 g/L). This can be accomplished by raising the pH set point to a range of 5.1-5.3, increasing the liquid flow through the system thus lowering the LRT to 15-20 hours, and by limiting the production of acid by limiting the available CO2 and/or ethanol or by lowering the culture metabolism through temperature reduction.

The production of acid depletes the ethanol concentration in the reactor. Since the culture is exhibiting decreased ethanol production while under these conditions, the ethanol concentration must be monitored to insure it is not excessively depleted. Ethanol may need to be added to the system or supplemented as the length of time without feed gas increases. During these experiments, ethanol concentration in the bioreactor has been depleted down to a concentration as low as 4g/L without detrimental effects to the culture.

Optionally, culture temperature plays vital role in this process as a way to control the metabolic rate of the cells. As the temperature is lowered, the cell's metabolic rate slows. That, in turn, slows the production of acid and the use of ethanol and CO2. Lowering the temperature when the reactor is without feed gas extends the length of time the culture can survive. Conversely, if the temperature is kept at 38° C. the acid production rate is at its highest and careful monitoring of the acid level and ethanol level is required to keep the culture healthy. Experiments have lowered the culture temperature to about 25 ° C., successfully maintaining the cell viability for about 30 hours without feed gas.

An embodiment of the present invention provides a delivery method of a controlled amount of CO2 comprising NaHCO3 addition. When sodium bicarbonate is introduced into an acid environment like the fermentation broth CO2 is produced as shown below in Equation 2. It is believed that this method of CO2 addition to the system is advantageous over sparging CO2 into the culture because the sodium bicarbonate not only adds CO2 but also increases the culture pH to about 5.1, helping to compensate for the system production of acid by balancing the free acid levels.

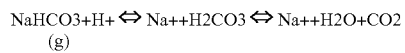

Equation 2

The conversion of ethanol to acid starts to take place almost immediately, or within seconds, after the loss of the feed gas. It is possible to prevent a quick and large buildup of acid at the start of the feed gas loss by stripping the dissolved CO2 present in the culture using a high N2 flow of about 400-450 mL/min. Nitrogen should be sparged through the culture for approximately 0-15 minutes as soon as possible after the feed gas flow is lost, the faster this is done the more advantageous it is for the present invention. Nitrogen flow within the first 5 minutes is an embodiment of the present invention. Once the inventory of dissolved CO2 has been removed, the NaHCO3 addition can be started using a controlled feed rate.

Using NaHCO3 addition to provide CO2 can increase the culture pH. If the cells remain active utilizing all of the sodium bicarbonate available, the pH should increase to about 5.1 then remain there. This is a desired secondary effect and should not be prevented. The slow and steady increase in pH will help to counter the rising acid production by keeping the free acid level in check. If however, the cell activity is compromised, the pH will increase beyond about 5.3 giving an indication that the culture may be denatured or otherwise functionally decreased.

When the feed gas is available, the sodium bicarbonate addition should be stopped and the mass transfer of the feed gas should be increased as quickly as possible, but taking care not to overwhelm the cells. Over a period of time of about 10-15 minutes, the agitation should be increased back to the same setting used prior to the feed gas loss and the feed gas flow rate increased back to about 50% of the original feed rate. Because of the availability of substrate and the high level of total acetyl the culture will steadily convert the acid back into ethanol. This will be reflected in an increase in pH and is expected. Changes to the fermentor's feed gas flow rate during this time should be made based on gas conversions as in any normal reactor operations.

Once the feed gas flow has been restarted, if all has gone well in preserving the cell's viability, the feed gas flow rate should be able to reach a normal operating setting within about 20-26 hours. The ethanol and acid concentrations can take longer to reach normal operating levels, about 26-72 hours.

A minimum agitation is required to maintain the temperature distribution throughout the bioreactor and to maintain the culture pH. Minimum agitation would be defined as just enough mixing to keep the liquid distributed. This can be about 50 rpm, or 40-60 rpm, as compared to high rates, such as 400 rpm, used during normal operations. This agitation in effect also keeps the cells suspended. It is believed that the cells should be suspended in order to provide constant contact with CO2 and ethanol to perform the needed reactions.

Acetogenic microorganisms require CO or H2 and CO2 in order to gain the necessary electrons and carbon for cell growth. During the periods of time without feed gas neither CO nor H2 are available for the cell growth process. It is believed that cell growth is suspended during those times of feed gas loss. It may be reasoned that a lower supply of feed gas could be used for culture survival during times in which the feed gas supply may be limited. Diminished amount of feed gas supplied provides the culture reversion to acid production mode. When the substrate feed rate is decreased, the culture will automatically stop the conversion of acid to ethanol causing an increased drop in the ethanol to acid ratio. Once this gas loss process is fully understood, it may be advisable that the best course of action is to stop the supply of feed gas completely during times of feed gas production difficulties rather that supplying a lower rate of substrate. If it is determined that it is preferable to lower the substrate feed rate, action must be taken to cope with the increase in acid. Such actions would involve increasing the liquid flow through the system to remove acid, increasing the culture pH to maintain a tolerable free acid level, and/or removing a large portion of the cells from the system to maintain a healthy gas uptake to cell ratio for minimal acid production.

TABLE 1

Medium Component and Their Concentrations in the 1x EtOH Medium

| Component/Ion | Added As | 1x EtOH Conc in Med (ppm) |
|---|---|---|
| NH4+ | NH4Cl/(NH4)2HPO4 | 838 |
| Fe | FeCl2•4H2O | 16.8 |
| Ni | NiCl2•6H2O | 0.198 |
| Co | CoCl2•6H2O | 0.991 |
| Se | Na2SeO3 | 0.0913 |
| Zn | ZnSO4•7H2O | 0.455 |
| Mo | Na2MoO4•2H2O | 0.238 |
| Mn | MnCl2•4H2O | 0.167 |
| B | H3BO3 | 1.05 |
| Cu | CuCl2•2H2O | 0.149 |
| W | Na2WO4•2H2O | 1.12 |
| K | KCl | 78.6 |
| Mg | MgCl2•6H2O | 59.8 |
| Na | NaCl | 78.7* |
| Ca | CaCl2•2H2O | 54.5 |
| Cysteine HCl | Cysteine HCl | 250 |
| PO4-2 | H3PO4/(NH4)2HPO4 | 816 |
| Pantothenic Acid | Pantothenic Acid | 0.025 |
| Biotin | Biotin | 0.020 |
| Thiamin | Thiamine | 0.050 |

*Na+ concentration is from NaCl only. It does not include Na+ from the other components such as Na2WO4•2H2O.
**Ca+2 concentration does not include calcium from pantothenic acid, calcium salt.

Table 2 details the culture parameters before and after the experiment such as pH, redox, ethanol and acetic acid. Generally, when the culture uses ethanol and CO2 for survival, the ethanol level decreases as the acid concentration and culture pH increases. Table 2 also lists the high measured level of free acid during those experiments as well as the number of hours after the end of the experiment to recover to the original gas feed rate. It should be remembered that a key component in culture survival during the feed gas loss is the maintenance of a free acid concentration <5.0 g/L. As acid is being produced, a higher culture pH and a faster acid removal rate is required to prevent acid inhibition. As acid is being produced, a higher culture pH or a faster acid removal rate is required to prevent acid inhibition.

Table 3 details the CO2 addition to the culture in mmol/min per gram of cells in the culture. The calculations were based on the feed rate of sodium bicarbonate and the total number of cells in the bioreactor. At 25 °C. a CO2 feed rate of 0.014 mmol/min·g was sufficient to sustain the culture for 12 hours without feed gas. When the experimental length of time was increased to 24 hours, an average CO2 feed rate of 0.034 mmol/min·g was required for healthy culture survival. Interestingly, when the culture temperature was increased to 38° C., the culture required a minimum CO2 feed rate of 0.114 mmol/min·g to maintain a healthy culture. At 38° C. the cell's metabolism is higher requiring more energy for survival, thus more ethanol conversion to acid.

Example 2

Survival of the culture for 17 and 24 hours without feed gas
Experimental conditions:
16.9 hr without feed gas
Temperature decreased to 25° C.
Medium addition was unchanged for the experiment
0.030 mmol/min CO2 feed rate per gram of cells
Permeate purge was used to hold in the cells
CO2 was NOT stripped from the culture broth at the start of the experiment Before the start of the experiment the culture cell density was 3.7 g/L; pH was 4.44; redox was −440 mV; CO and H2 uptake was 5.0 and 1.2 mmol/min respectively; CO and H2 conversions were 86 and 40% respectively; ethanol was 23.5 g/L; and acid was 3.9 g/L.

At t=9511.6 hours, the feed gas flow rate was decreased from 474 mL/min to 53 mL/min. The agitation was dropped from about 400 to about 50 rpm, and the temperature set point on the reactor was decreased from 38 to 25° C. within about 12 minutes. Once cooling was done, 38.5 g/L sodium bicarbonate as started at 0.57 mL/min providing a 0.030 mmol/min per gram of cells CO2 feed rate; the feed gas flow was stopped; a permeate purge was started at 1.95 mL/min, and the medium flow was kept at 1.37 mL/min. Nitrogen was slowly added to the reactor headspace to prevent a vacuum from forming in the reactor. The culture was left in that condition for 16.9 hours.

During the experiment liquid samples were taken approximately every 2 hours to monitor culture pH, cell density, products and cell morphology. The culture pH increased steadily throughout the experiment to reach 5.07 toward the end of the experiment. The ethanol concentration decreased steadily from 23.5 to 7.0 g/L by the end of the experiment. The total acetyl concentration increased steadily from 3.9 to 8.2 g/L. Approximately 12 hours into the experiment the culture morphology showed only 5-10% of the cells were grainy or hollow bodies. The cell length was average with mild to no warping or bending.

At t=9528.5 hrs, the temperature set point on the reactor was increased back to about 38° C.; the feed gas was restarted at about 53 mL/min; Medium B and permeate purge were stopped; and the N2 flow into the reactor headspace was stopped. When the temperature reached about 28.0° C., the feed gas flow rate was increased to 143 mL/min. At about 30.0° C. the feed gas flow was increased again to 236 mL/min, or 50% or the original gas flow rate. At about 32.0° C., the agitation was increased to 200 rpm. At about 34° C. the agitation was increased to about 400 rpm.

Initial conversions about 40 minutes after the increase in gas, agitation and temperature were good at 47% H2 and 88% CO. Approximately 15 min later the conversions were still very good at 47% H2 and 87% CO. Gas flow rate increases were started right away. It took about 18.3 hours to reach the maximum gas flow used prior to the start of the experiment. As the gas flow rate was increased, the pH continued to drop reaching about 4.60 within about 18.3 hours. The ethanol increased back to 20.0 g/L 40.6 hours after the end of the experiment, and the acid dropped back to 3.4 g/L after 24.9 hours.

Example 3

Experimental Conditions
About 24 hr without feed gas
Temperature dropped to about 25° C.
Medium addition was unchanged for the experiment
0.035 mmol/min CO2 feed rate per gram of cells
Permeate purge was used to hold in the cells
CO2 was NOT stripped from the culture broth at the start of the experiment Before the start of the experiment the culture cell density was about 3.2 g/L; pH was about 4.50; redox was about −425 mV; CO and H2 uptake was 4.7 and 1.5 mmol/min respectively; ethanol was about 17.7 g/L; and acid was about 2.93 g/L.

At t=1888 hours, the feed gas flow rate was decreased from about 474 mL/min to 53 mL/min. The agitation was dropped from about 400 to about 50 rpm, and the temperature set point on the reactor was decreased from about 38 to about 25° C. in about 14 minutes. Once cooling was done, the sodium bicarbonate addition was started using a about 38.5 g/L NaHCO3 flow of 0.58 mL/min providing a CO2 feed rate of 0.035 mmol/min per gram of cells; the feed gas flow was stopped; a permeate purge was started at 1.81 mL/min, and the medium flow was kept at 1.30 mL/min. Nitrogen was slowly added to the reactor headspace to prevent a vacuum from forming in the reactor. The culture was left in that condition for about 24 hours.

Approximately 15.5 hours into the experiment the reactor condition provided: cell density of about 2.4 g/L; pH of about 4.96; EtOH of about 6.06 g/L; and acid was about 7.87 g/L. The cell morphology showed about 5-10% of the cells were grainy or almost grainy. Due to the low ethanol concentration left in the reactor, at t=1904 hours, 115 mL of Gem Clear grain alcohol was added to 9 L of medium A for an ethanol concentration of about 10 O/L. The medium feed rate remained the same providing an ethanol feed rate of 0.037 mmol/min per gram of cells.

At the end of the 24 hours, the culture condition provided: cell density of about 2.9 g/L; pH of about 5.04; EtOH of about 4.10 g/l; and acid was about 8.68 g/L. The cell morphology showed about 10-15% of the cells had turned grainy or almost grainy.

At t=1912 hrs, the temperature set point on the reactor was increased back to about 38° C.; the feed gas was restarted at about 53 ml/min; Medium B and permeate purge were stopped; and the N2 flow into the reactor headspace was stopped. Medium was changed to a normal 1× EtOH medium with no ethanol added. The feed gas and agitation were increased at regular intervals as the temperature increased stepwise. When the temperature reached about 28.0° C., the feed gas flow rate was increased to about 179 mL/min. At about 30.0° C. the feed gas flow was increased again to about 248 ml/min, or about 50% or the original gas flow rate. At about 32.0° C., the agitation was increased to about 200 rpm. At about 34° C. the agitation was increased to about 400 rpm.

As an embodiment, initial conversions about 35 minutes after the increase in gas, agitation and temperature were at 60% H2 and 84% CO. As an embodiment, approximately 15 min later the conversions provided: 62% H2 and 91% CO. Gas flow rate increases were introduced immediately. In this case, it took about 19.5 hours to reach the maximum gas flow used prior to the start of the experiment.

Example 4

Experimental Conditions:
23.5 hr without feed gas
Temperature dropped to 25° C.
Medium addition was reduced to half of the normal flow; the cysteine concentration was doubled in the medium
0.039 mmol/min CO2 feed rate per gram of cells
Permeate purge was used to hold in the cells
CO2 was NOT stripped from the culture broth at the start of the experiment In an embodiment, the 24 hour gas loss experiment showed that the culture can survive very well for about 24 hours without feed gas while providing 0.035 mmol/min CO2 addition per gram of cells. The medium and sodium bicarbonate flows into the reactor during the experiment required about 2.6 L of permeate to be removed to prevent cell loss due to washout. That is slightly more than the 2.4 L of culture volume. In lab scale that ratio of required liquid flow to culture volume is well tolerated. However, on an industrial scale, the waste water amount must be monitored and, if needed, decreased. In this experiment all parameters were kept the same as the previous, experiments except the medium flow rate was reduced by half to reduce the amount of permeate purge that is required. There have been some indications in past experiment that suggest that a reduction in the cysteine feed rate may interfere with the experiment, so during this experiment the cysteine concentration in medium was doubled to retain the cysteine feed rate.

Before the start of the experiment the culture cell density was about 2.5 g/L; pH was about 4.50; redox was about −440 mV; CO and H2 uptake was about 4.8 and about 1.2 mmol/min respectively; ethanol was about 21.3 g/L; and acid was about 2.96 g/L.

At t=2008.5 hours, the feed gas flow rate was decreased from 474 mL/min to 53 mL/min. The agitation was dropped from about 400 to about 50 rpm, and the temperature set point on the reactor was decreased from 38 to 25° C. within 13 minutes. Once cooling was done, the sodium bicarbonate addition was started using a 38.5 g/L NaHCO3 solution at 0.57 ml/min; the feed gas flow was stopped; a permeate purge was started at 1.20 ml/min, and the medium flow was reduced to 0.68 ml/min. Nitrogen was slowly added to the reactor headspace to prevent a vacuum from forming in the reactor. The cysteine concentration was increased to 5 g/L in medium A. The CO2 was provided at 0.039 mmol/min per gram of cells. The culture was maintained in that condition for 24 hours.

During the experiment liquid samples were taken approximately every 2 hours to monitor culture pH, cell density, products and cell morphology. As expected the pH increased steadily throughout the experiment to reach 5.14 at the end of the experiment. The ethanol concentration decreased steadily from 21.3 to 6.03 g/L by the end of the experiment. The total acetyl concentration increased steadily from 2.96 to 10.38 g/L. After about 24 hours the culture morphology showed about 10-20% of cells were grainy or almost grainy.

At t=2032 hrs, the temperature set point on the reactor was increased back to about 38° C.; the feed gas was restarted at about 53 ml/min; sodium bicarbonate addition and permeate purge were stopped; and the N2 flow into the reactor headspace was stopped. Medium flow rate was increased back to 1.37 ml/min. As the culture was heating the feed gas flow was increased back to 248 ml/min and the agitation was raised to about 400 rpm stepwise.

Initial conversions about 30 minutes after the increase in gas, agitation and temperature were at 50% H2 and 87% CO. Gas flow rate increases were started right away. It took about 24 hours to reach the maximum gas flow used prior to the start of the experiment.

Example 5

Minimization of the CO2 feed rate while at 25° C., 12 hour culture survival
  Experimental Conditions:
  12 hr without feed gas
  Temperature dropped to 25° C.
  Medium addition was unchanged for the experiment
  0.014 mmol/min CO2 feed rate per gram of cells
  Permeate purge was used to hold in the cells
  CO2 was NOT stripped from the culture broth at the start of the experiment This experiment evaluates the minimum CO2 addition rate needed to sustain the culture for 12 hours at 25°. As an embodiment, NaHCO3 solution used as Medium B was decreased in concentration while keeping all other experimental parameters the same. In this experiment the NaHCO3 concentration was dropped to about 19.3 g/L providing a CO2 feed rate of about 0.014 mmol/min CO2 per gram of cells in the reactor. This is a low feed rate with culture survival.

Before the start of the experiment the culture cell density was about 4.0 g/L; pH was about 4.43; redox was about −430 mV; CO and H2 uptake was about 4.9 and about 1.3 mmol/min respectively; CO and H2 conversions were about 86 and about 44% respectively; ethanol was about 18.9 g/L; and acid was about 3.8 g/L.

At 2015, t=9580.7 hours, the feed gas flow rate was decreased from about 474 mL/min to about 53 mL/min. The agitation was dropped from about 400 to about 50 rpm, and the temperature set point on the reactor was decreased from about 38 to about 25° C. within about 12 minutes. Once cooling is accomplished, the sodium bicarbonate flow was started at 0.56 mL/min; the feed gas flow was stopped; a permeate purge was started at 1.96 mL/min, and the medium flow was kept at 1.36 mL/min. Nitrogen was slowly added to the reactor headspace to prevent a vacuum from forming in the reactor. The culture was maintained in that condition for about 12 hours.

During the experiment liquid samples were taken approximately every 2 hours to monitor culture pH, cell density, products and cell morphology. Throughout the experiment the pH increased steadily throughout the experiment to reach about 4.72 toward the end of the experiment. The ethanol concentration decreased steadily from about 18.9 to about 10.7 g/L by the end of the experiment. The total acetyl concentration increased steadily from about 3.8 to about 6.0 g/L. The cell density dropped from about 4.0 to about 2.8 g/L. After about 12 hours the culture morphology provided about 95+% of the cells were average to slightly long in length with only minimal warping or bending and only an occasional grainy cell or hollow body.

At t=9592.7hrs, the temperature set point on the reactor was increased back to about 38° C.; the feed gas was restarted at about 53 mL/min; Medium B and permeate purge were stopped; and the N2 flow into the reactor headspace was stopped. While the culture warmed over the next 15 minutes, the feed gas flow rate and agitation were increased stepwise. When the temperature reached about 28.0° C., the feed gas flow rate was increased to about 178 mL/min. The pH of the culture was slowing dropping indicating culture activity. At about 30.0° C. the feed gas flow was increased again to 236 mL/min, or 50% or the original gas flow rate. At about 32.0° C., the agitation was increased to about 200 rpm. At about 34° C. the agitation was increased to about 400 rpm.

Initial conversions 50 minutes after the increase in gas, agitation and temperature provided about 53% H2 and about 89% CO. Gas flow rate increases were started immediately. It took 14.6 hours to reach the maximum gas flow used prior to the start of the experiment. As the gas flow rate was increased, the ethanol concentration increased back to about 23.7 g/L 49.4 hours, and the acid dropped back to about 3.5 g/L 9.3 hours after experiment end.

Example 6

Minimization of the CO2 feed rate while at 38° C., 6 hour culture survival
  Experiment Conditions:
  6 hr without feed gas
  Temperature remained at 38° C.
  Medium addition was unchanged for the experiment
  0.114 mmol/min CO2 feed rate per gram of cells
  Permeate purge was used to hold in the cells
  N2 used to strip CO2 from the culture broth at the start of the experiment Before the start of the experiment the culture cell density was about 2.76 g/L; pH was about 4.60; redox was about −440 mV; CO and H2 uptake was about 4.5 and about 1.2 mmol/min respectively; ethanol was about 19.0 g/L; and acid was about 2.43 g/L.

At t=3080.5 hrs, the feed gas flow rate was decreased from about 475 ml/min to about 53 ml/min then turned off. A high N2 flow was started through the feed gas sparger while the agitation was still at about 400 rpm for about 3 minutes to strip the CO2 from the culture. While stripping the CO2, the pH control was turned off to prevent any sodium bicarbonate addition. After about 3 minutes, the N2 flow was dropped and the N2 inlet was changed to the headspace rather than the sparger. The agitation was dropped from about 400 to about 50 rpm. CO2 addition was started at about 0.82 mL/min using about 77 g/L NaHCO3 to provide about 0.11 4 mmol/min CO2 per gram of cells in the reactor. The medium flow rate was left at about 1.34 mL/min, and a permeate purge flow of 2.25 ml/min was started.

The experiment was stopped after 6 hours at t=3086.5 hours due to high acid. Sodium bicarbonate addition, permeate purge and N2 addition to the headspace were stopped. The feed gas flow was restarted at 53 mL/min. The feed gas and agitation were increased at about the same intervals as is used to increase gas and agitation when the culture is warming to about 38° C. in the previous experiments. Two minutes after the experiment was stopped the feed gas flow was increased to about 170 mL/min. About four minutes after the experiment was stopped the feed gas flow was increased to about 248 mL/min (50% of the original gas flow rate). About six minutes after the experiment was stopped the agitation was increased to 200 rpm. About eight minutes after the experiment was stopped the agitation was increased to about 400 rpm.

After about 6 hours with CO2 addition and low agitation, the pH was about 5.08. A liquid analysis showed the products were about 10.4 g/L ethanol and about 8.21 g/L acid. The culture morphology showed about 3% of the cells were grainy with an additional about 22% were almost grainy.

Initial conversions about 30 minutes after the experiment was stopped were about 47% H2 and about 87% CO. Gas flow rate increases were started right away. The original feed gas flow rate was reached at t=3108 hours, or about 21.5 hours after the experiment ended.

TABLE 2

Culture Parameters in Gas Loss Experiments at about 25 C. and about 38 C. Where Culture was restarted using Agitation and at Least 50% of the Original GFR

| Run | Experimental Culturue Temp (C.) | Bicarbonate Conc (g/L) | # Hrs w/o Feed Gas | Δ in EtOH Before Exp (g/L) | Δ in EtOH End of Exp (g/L) | Δ in Hac Before Exp (g/L) | Δ in Hac End of Exp | Δ in pH Before Exp | Δ in pH End of Exp | Δ in Redox Before Exp (mV) | Δ in Redox End of Exp | Max Free Acid Reached (g/L) | Recovery Time # Hrs to Reach Original GFR |
|---|---|---|---|---|---|---|---|---|---|---|---|---|---|
| 1 | 25 | 77 | 8 | 21.01 | 10.74 | 4.41 | 9.36 | 4.48 | 4.93 | −425 | −325 | 4.1 | 29.2 |
| 2 | 25 | 38.5 | 16.9 | 23.51 | 7.03 | 3.91 | 8.24 | 4.44 | 5.07 | −440 | −245 | 3.5 | 18.3 |
| 3 | 25 | 19.25 | 12 | 18.95 | 9.91 | 3.83 | 5.78 | 4.43 | 4.72 | −430 | −265 | 3.2 | 14.6 |
| 4 | 25 | 9.625 | 12.25 | 20.28 | 11.92 | 3.54 | 2.61 | 4.53 | 5.12 | −440 | −240 | 2.3 | 35.2 |
| 5 | 25 | 14.63 | 12.25 | 17.89 | 11.10 | 5.52 | 4.40 | 4.53 | 5.04 | −440 | −370 | 1.5 | 35.6 |
| 6 | 25 | 38.5 | 24 | 17.70 | 4.10 | 2.93 | 8.68 | 4.50 | 5.04 | −425 | −305 | 3.1 | 19.5 |
| 7 | 25 | 38.5 | 23.5 | 21.30 | 6.03 | 2.96 | 10.38 | 4.50 | 5.14 | −440 | −320 | 3.5 | 24 |
| 8 | 38 | 77 | 4 | 21.30 | 9.88 | 3.28 | 14.60 | 4.56 | 5.26 | −445 | −340 | 3.4 | 13.5 |
| 9 | 38 | 77 | 6.75 | 23.20 | 7.25 | 3.15 | 14.50 | 4.47 | 5.53 | −430 | −280 | 3.2 | 19 |
| 10 | 38 | 77 | 6.5 | 20.44 | 7.04 | 2.86 | 12.79 | 4.53 | 5.30 | −440 | −235 | 3.1 | 20.75 |
| 11 | 38 | 77 | 7 | 22.20 | 8.77 | 3.40 | 14.10 | 4.48 | 5.15 | −435 | −275 | 4.0 | 28 |
| 12 | 38 | 77 | 6 | 19.00 | 10.4 | 2.43 | 8.21 | 4.60 | 5.08 | −440 | −270 | 2.6 | 21.5 |
| 13 | 38 | 77 | 8.5 | 20.15 | 7.5 | 1.75 | 12.12 | 4.53 | 5.2 | −430 | −200 | 3.4 | 30.5 |

TABLE 3

Table 3. Calculated CO2 Feed Rate per Gram of Cells in the Reactor (mmol/min g) for Bicarbonate Addition, Feed Gas Loss Experiments w/Known CO2 Addition Rates

| Run | Culture Temp (C.) | NaHCO3 Conc (g/L) | NaHCO3 Flow Rate (ml/min) | CO2 Feed Rate (mmol/min) | Cell Density (g/L) | Culture Vol (L) | CO2 Feed Rate per Gram of Cells (mmol/min g) | Exp Time Length (Hrs) | Recovery Time (Hrs) |
|---|---|---|---|---|---|---|---|---|---|
| 1 | 25 | 77 | 0.57 | 0.5224 | 3.64 | 2.35 | 0.0610 | 8 | 29.2 |
| 2 | 25 | 38.5 | 0.57 | 0.2612 | 3.71 | 2.325 | 0.0303 | 17 | 18.3 |
| 3 | 25 | 19.25 | 0.56 | 0.1283 | 4.02 | 2.325 | 0.0137 | 12 | 14.6 |
| 4 | 25 | 9.625 | 0.57 | 0.0653 | 3.25 | 2.3 | 0.0087 | 12 | 35.2 |
| 5 | 25 | 14.63 | 0.58 | 0.1010 | 3.97 | 2.375 | 0.0107 | 12 | 35.6 |
| 6 | 25 | 38.5 | 0.58 | 0.2658 | 3.20 | 2.4 | 0.0347 | 24 | 19.5 |
| 7 | 25 | 38.5 | 0.57 | 0.2612 | 2.69 | 2.5 | 0.0388 | 24 | 24 |
| 8 | 38 | 77 | 3.18 | 2.9147 | 3.12 | 2.45 | 0.3815 | 4 | 13.5 |
| 9 | 38 | 77 | 1.65 | 1.5123 | 2.48 | 2.45 | 0.2492 | 6.75 | 19 |
| 10 | 38 | 77 | 1.4 | 1.2832 | 2.98 | 2.35 | 0.1834 | 6.5 | 20.75 |
| 11 | 38 | 77 | 1 | 0.9166 | 2.84 | 2.4 | 0.1347 | 7 | 28 |
| 12 | 38 | 77 | 0.82 | 0.7516 | 2.76 | 2.4 | 0.1135 | 6 | 21.5 |
| 13 | 38 | 77 | 0.92 | 0.8432 | 2.71 | 2.4 | 0.1298 | 8.5 | 30.5 |

TABLE 4

Table 4. CO2 Feed Rate, EtOH Uptake Rate and Acid Production Rate During the Feed Gas Loss Experiments

| Run | Experiment Temperature (° C.) | CO2 Feed Rate (mmol/min g) | Acid Production (mmol/min g) | EtOH Consumption (mmol/min g) | Experiment Length of Time (hrs) |
|---|---|---|---|---|---|
| 1 | 25 | 0.0610 | 0.0816 | 0.0442 | 8 |
| 2 | 25 | 0.0306 | 0.0419 | 0.0310 | 17 |
| 3 | 25 | 0.0140 | 0.0263 | 0.0211 | 12 |
| 4 | 25 | 0.0346 | 0.0451 | — | 24.0 |
| 5 | 25 | 0.0387 | 0.0546 | 0.0504 | 24.0 |
| 6 | 38 | 0.382 | 0.285 | 0.096 | 4.0 |
| 7 | 38 | 0.223 | 0.295 | 0.222 | 6.75 |
| 8 | 38 | 0.187 | 0.192 | 0.131 | 6.5 |
| 9 | 38 | 0.142 | 0.196 | 0.123 | 7.0 |
| 10 | 38 | 0.113 | 0.136 | 0.086 | 6.0 |
| 11 | 38 | 0.130 | 0.166 | 0.100 | 8.5 |

Example 7

Comparative Example

An Exemplary Method of the Present Invention

A synthesis or waste gas containing CO and/or carbon dioxide/gaseous hydrogen is continuously introduced into a stirred tank bioreactor containing a strain of C. ljungdahlii, along with a conventional liquid medium containing vitamins, trace metals and salts.

During method start-up using a culture inoculum of 10% or less the reactor is operated with a batch liquid phase, where the liquid medium is not fed continuously to the reactor. The liquid phase in the reactor thus consists of a batch of nutrient medium with a nominal concentration of limiting nutrient, either calcium pantothenate or cobalt. Alternatively, a rich medium containing yeast extract, trypticase or other complex nutrients can also be employed.

Ideally, the gas phase at start-up is CO2 free and contains excess $H_2$. The gas rate and agitation rate are kept at low levels (less than 500 rpm in a New Brunswick Scientific Bioflo® fermentation bioreactor) to yield CO and $H_2$ in slight excess, but at the same time, avoiding CO substrate inhibition. In a one-liter laboratory New Brunswick Scientific Bioflo® fermentation bioreactor, as an example, where the feed gas composition is 63% $H_2$, 32% CO and 5% $CH_4$, the agitation rate to initiate start-up is 400 rpm and the gas rate is 20 ml/min. The cause of ethanol production during start-up is excess $H_2$; limitation on nutrients occurs later. Thus, excess liquid nutrients (pantothenate, cobalt) are actually present during start-up to avoid unwanted culture acclimation to low nutrients.

As the fermentation proceeds over a period of several hours after inoculation, CO2 is produced from the conversion of CO, and $H_2$ is consumed along with the $CO_2$, which is a signal to nominally increase the agitation rate to avoid gas mass transfer limitation. In the New Brunswick Scientific Bioflo® CSTR, the exit gas is 25% CO, 67% $H_2$, 2% $CO_2$, and 6% $CH_4$. If the agitation rate is increased too fast, CO substrate inhibition occurs, as evidenced by a decrease in methane concentration after an increase in agitation. Thus the agitation rate might typically be increased by 200 rpm in 24 hours. This procedure of monitoring $CO_2$ production (or $H_2$ conversion) while nominally increasing agitation rate occurs at a relatively rapid rate until the target agitation rate is reached. A typical target agitation rate in the New Brunswick Scientific Bioflo® fermentation bioreactor is 900 rpm. During this time of increasing agitation rate in batch liquid culture, cell production instead of product formation is of utmost importance. Thus, cell concentrations of about 1.5 g/L are attained, while typical product concentrations are 10 g/L ethanol and 2 g/L acetate from the batch culture.

Once the target agitation rate is reached, the system is allowed to grow to maximum $H_2$ uptake. It is desirable to have very high $H_2$ exit concentrations (typically>60%) to assure ethanol production while limiting acetic acid production. The liquid medium feed is then turned on (for systems having batch inoculation from stock culture) to initiate continuous liquid feed and the gas feed rate is increased toward the target flow rate. In the laboratory New Brunswick Scientific Bioflo® fermentation bioreactor the liquid feed rate is typically 0.5 mL/min, while the gas flow rate is increased by 10 to 15% every 24 hours toward a target rate of 125 mL/min.

It is important to provide excess $H_2$ in the feed gas to avoid excess acetic acid production. As the gas flow rate is increased, cell production increases until the reactor is eventually limited on liquid phase nutrients (calcium pantothenate or cobalt) as evidenced by a small drop in $H_2$ conversion, at the target productivity. In the New Brunswick Scientific Bioflo® CSTR, this is recognized by a 10% drop in $H_2$ conversion at a target productivity of 20 g/L.day.

The production method and reactor system are then maintained at a steady state producing 15 to 35 g/L ethanol and 0 to 5 g/L acetate as products, with only occasional small adjustments in limiting nutrients, liquid rates and gas rate. Typical steady state conditions in the laboratory New Brunswick Scientific Bioflo® fermentation bioreactor without cell recycle, are a gas retention time (gas flow rate/reactor liquid volume) of 20 minutes, a liquid retention time (liquid flow rate/reactor liquid volume) of 30 hours and an agitation rate of 900 rpm, yielding CO conversions of 92% and $H_2$ conversions of 60% with pantothenate limitation.

In an embodiment of this method in which cell recycle is added to the reactor system, it is added at this time along with an adjustment in gas rate (increase) and nutrient concentration (decrease). With cell recycle in the New Brunswick Scientific Bioflo® CSTR, the gas retention time is typically 8 minutes, the liquid retention time is 12 hours, the cell retention time is 40 hours and the agitation rate is 900 rpm. These conditions typically yield a CO conversion of 92% and a $H_2$ conversion of 50% with pantothenate limitation.

Example 8

Comparative Example:

Recovery from Severe Method Upset

A CSTR with cell recycle containing C. ljungdahlii, strain C-01 being continuously fed gas and liquid nutrients and producing 15-35 g/L ethanol and 0-5 g/L acetate at a steady state is upset due to unforeseen changes in method conditions, e.g., mechanical problems in the reactor. Upset to the reactor system can either be minor, such as a brief increase in the gas rate which causes short-term substrate inhibition, or major, such as a longer term increase in the gas rate which eventually leads to increased acetic acid production and more severe molecular acetic acid product inhibition.

Short-term upsets are easily corrected by merely readjusting the upset parameter (for example, lowering the gas rate to its original level) and monitoring the progress of the reactor to assure that the upset has not led to a longer-term problem.

However, acetic acid product inhibition is a more severe problem. If excess molecular acetic acid is produced by the culture as a result of long term substrate inhibition, excess nutrient addition, $CO_2$ accumulation or mechanical problems of many types, the problem that led to the excess acetic acid must first be corrected. The excess acetic acid, which quickly leads to product inhibition, is then cleared from the system by increasing the liquid rate to wash the acetic acid (and unfortunately ethanol) from the system. Once the acetate level is below 3-5 g/L, the liquid rate is reset and the reactor is placed back under either excess $H_2$ feed, or vitamin or cobalt limitation (with or without cell recycle). Bringing the reactor back involves reducing the gas rate to avoid substrate inhibition and/or agitation rate before cell washout and lysis takes place. The agitation rate or gas rate is then increased.

In one specific example, a CSTR with cell recycle containing C. ljungdahlii, strain C-01 that was producing ethanol and acetic acid from CO, $CO_2$ and $H_2$ began producing acetic acid in response to a mechanical problem. The 2100 ml reactor was fed gas containing 62% $H_2$, 31% CO and 7% $C_2H_6$ at a gas retention time of 15 minutes, and was operating with an agitation rate of 600 rpm and a pH of 4.86. The liquid retention time was 23 hours and the cell retention time was 68 hours. B-vitamin solution (an aqueous mixture of 50.5 mg/l calcium pantothenate, 20.6 mg/L d-biotin and 50.6 mg/L thiamine HCl) was present in the liquid nutrient medium containing salts and vitamins at a concentration of 0.4 ml vitamin solution per liter of medium (see Table 2). The ethanol concentration fell to 7 g/L, while the acetate concentration rose to 7 g/L, conditions that are neither stable for operating the reactor nor economical for ethanol production. The cell concentration was 2.4 g/L, the CO conversion was 85% and the $H_2$ conversion was 25%.

The strategy used in recovering the reactor consisted of first dramatically reducing the gas feed rate to the reactor, followed by gradual recovery of the reactor in the presence of excess $H_2$. The liquid rate to the reactor was not reduced to clear product inhibition in this example because the acetate concentration was not exceedingly high. Instead, the acetate concentration was allowed to more gradually drop to non-inhibiting levels with the reduction in gas flow rate and subsequent operation in the presence of excess $H_2$. The specific procedure in recovering the reactor is discussed below.

Cell recycle was turned off and the gas rate was dramatically reduced by 70% to a gas retention time of 62 minutes, while only slightly adjusting the liquid retention time from 23 to 30 hours (t=0). The vitamin concentration in the medium was not changed. With this change in gas rate the CO conversion increased to 98% and the $H_2$ conversion increased to 80%. More importantly the system had excess $H_2$ present, as evidenced by the decrease in $CO_2$ in the outlet gas from 19 to 5%. With the onset of excess $H_2$, the acetate concentration fell while the ethanol concentration increased. At t=66 hr (66 hr after turning off cell recycle), for example, the acetate concentration had fallen to 4 g/L and the ethanol concentration had risen slightly to 7.5 g/L.

The presence of excess $H_2$ (and the lowered acetate concentration) permitted subsequent increases in as rate, first slowly and then at a faster rate. By t=215 hr the gas retention was 29 minutes, the ethanol concentration was 12 g/L and the acetate concentration was 3 g/L. The ethanol productivity was 8 g/L·day. $CO_2$ was present in the outlet gas at 6%, the CO conversion was 98% and the $H_2$ conversion was 80%. By t=315 hr, the ethanol concentration was 16 g/L and the acetate concentration was 4 g/L, again with good gas conversions, and a gas retention time of 20 minutes. The ethanol productivity was 11 g/L·day. By t=465 hr, the ethanol concentration had reached 20 g/L, with 3.5-4 g/L acetate also present. The ethanol productivity was 16 g/L·day. The gas retention time had been dropped to 16 minutes, with CO and $H_2$ conversions of 95 and 73%, respectively. These conditions were maintained for nearly 200 hours of continuous operation, demonstrating that the reactor system had recovered its ability to produce ethanol and had essentially retained the previous operating conditions.

All published documents are incorporated by reference herein. Numerous modifications and variations of the present invention are included in the above-identified specification and are expected to be obvious to one of skill in the art. Such modifications and alterations to the compositions and methods of the present invention are believed to be encompassed in the scope of the claims appended hereto.

The invention claimed is:

1. A method for sustaining alcohol producing microorganism culture containing at least one acetogenic bacteria wherein said microorganism culture comprising one or more strains selected from *Clostridium, Moorella, Carboxydothermus* and their genetic modifications in a syngas fermentation reactor at an operating temperature in decreased concentration or absence of syngas comprising: adding carbon dioxide and optionally adding alcohol; maintaining free acetic acid concentration to less than 5 g/L free acetic acid; consuming alcohol in existing solution of said fermentation reactor; performing the above mentioned steps within 30 minutes of said decreased concentration or absence of syngas; comprising a ratio of less than 0.77 consumed alcohol to initial alcohol; and subsequently recovering the microorganism culture to produce alcohol; wherein said alcohol comprises one or more of ethanol and butanol.

2. The method of claim 1 wherein said sustaining microorganism culture comprises duration of about 0-30 hours.

3. The method of claim 1, wherein pH of the microorganism culture is maintained in the range of about 3.5-5.6.

4. The method of claim 1, wherein a bicarbonate solution is added to control pH of the microorganism culture.

5. The method of claim 1, wherein optionally removing said carbon dioxide from the said reactor.

6. The method of claim 1, optionally adding nutrients to said reactor.

7. The method of claim 1, wherein alcohol comprises one or more of ethanol and butanol.

8. The method of claim 1, optionally changing temperature from said operating temperature to between 0-25 degrees C. if temperature is not between 0-25 degrees C.

9. The method of claim 1, optionally adding water to said reactor.

10. The method of claim 1, optionally adding water to said reactor comprising: fresh water, make-up water, recycle water, distilled water, deionized water or their combinations.

11. The method of claim 1 wherein said microorganism culture is returned to pre suspension conditions comprising addition of syngas.

12. The method of claim 1 wherein optionally removing permeate.

13. The method of claim 1 wherein optionally purging said reactor with inert gas.

14. The method of claim 1 wherein optionally maintaining low agitation to keep solids in suspension.

15. A method for preventing rapid loss of alcohol producing microorganism culture containing at least one acetogenic bacteria wherein said microorganism culture comprising one or more strains selected from *Clostridium, Moorella, Carboxydothermus* and their genetic modifications in a syngas fermentation reactor in decreased concentration or absence of syngas comprising: decreasing temperature from operating temperature to between 0-25 degrees C. if said operating temperature is not between 0-25 degrees C.; maintaining free acetic acid concentration to less than 5 g/L free acetic acid; consuming alcohol in existing solution of said fermentation reactor; performing the above mentioned steps within 30 minutes of said decreased concentration or absence of syngas; comprising a ratio of less than 0.77 consumed alcohol to initial alcohol; and subsequently recovering the microorganism culture to produce alcohol; wherein said alcohol comprises one or more of ethanol and butanol.

16. A method for sustaining alcohol producing microorganism culture containing at least one acetogenic bacteria wherein said microorganism culture comprising one or more strains selected from *Clostridium, Moorella, Carboxydother-*

*mus* and their genetic modifications in a syngas fermentation reactor due to decreased concentration or absence of syngas in feed gas supply comprising: decreasing temperature from operating temperature to between 0-25 degrees C. if said operating temperature is not between 0-25 degrees C.; maintaining free acetic acid concentration to less than 5 g/L free acetic acid; consuming alcohol in existing solution of said fermentation reactor; performing the above mentioned steps within 30 minutes of said decreased concentration or absence of syngas; comprising a ratio of less than 0.77 consumed alcohol to initial alcohol; and subsequently recovering the microorganism culture to produce alcohol; wherein said alcohol comprises one or more of ethanol and butanol.

\* \* \* \* \*